(12) United States Patent
Bushman et al.

(10) Patent No.: US 10,058,576 B2
(45) Date of Patent: Aug. 28, 2018

(54) COMPOSITIONS AND METHODS COMPRISING A DEFINED MICROBIOME AND METHODS OF USE THEREOF

(71) Applicant: THE TRUSTEES OF THE UNIVERSITY OF PENNSYLVANIA, Philadelphia, PA (US)

(72) Inventors: Frederic Bushman, Rose Valley, PA (US); Gary Wu, Ardmore, PA (US); James Lewis, Moorestown, PA (US); Mark Goulian, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 36 days.

(21) Appl. No.: 15/090,609

(22) Filed: Apr. 4, 2016

(65) Prior Publication Data

US 2016/0243175 A1    Aug. 25, 2016

Related U.S. Application Data

(63) Continuation-in-part of application No. PCT/US2014/059166, filed on Oct. 3, 2014.

(60) Provisional application No. 61/974,686, filed on Apr. 3, 2014, provisional application No. 61/886,268, filed (Continued)

(51) Int. Cl.
| | | |
|---|---|---|
| *A61K 35/747* | (2015.01) | |
| *A61K 35/745* | (2015.01) | |
| *C12N 1/20* | (2006.01) | |
| *A61K 35/744* | (2015.01) | |
| *A61K 35/74* | (2015.01) | |
| *A61K 9/48* | (2006.01) | |
| *A61K 45/06* | (2006.01) | |

(Continued)

(52) U.S. Cl.
CPC ........... *A61K 35/747* (2013.01); *A61K 35/74* (2013.01); *A61K 35/742* (2013.01); *A61K 35/744* (2013.01); *A61K 35/745* (2013.01); *A61K 45/06* (2013.01); *C12N 1/20* (2013.01); *A61K 9/19* (2013.01); *A61K 9/48* (2013.01)

(58) Field of Classification Search
None
See application file for complete search history.

(56) References Cited

U.S. PATENT DOCUMENTS

| | | |
|---|---|---|
| 2007/0269403 A1 | 11/2007 | Halow |
| 2012/0058094 A1 | 3/2012 | Blaser et al. |
| 2012/0107291 A1 | 5/2012 | Burcelin et al. |

FOREIGN PATENT DOCUMENTS

| | | |
|---|---|---|
| WO | 2012122478 A1 | 9/2012 |
| WO | 2012/142605 A1 | 10/2012 |
| WO | 2012159023 A2 | 11/2012 |

OTHER PUBLICATIONS

Lesbros-Pantoflicka, Draahoslava; et al; "Helicobacter pylori and Probiotics" The Journal of Nutrition, 137, 812S-818S, 2007.*
(Continued)

*Primary Examiner* — David W Berke-Schlessel
(74) *Attorney, Agent, or Firm* — Kathleen D. Rigaut; Dann, Dorfman, Herrell and Skillman, P.C.

(57) ABSTRACT

The invention features the use of a defined microbial consortia for the replacement of a gut microbiome associated with disease. In particular, the invention provides for the treatment of hyperammonemia, *Clostridium difficile* colitis, hepatic encephalopathy associated with cirrhosis, and inflammatory bowel disease.

9 Claims, 29 Drawing Sheets

Related U.S. Application Data on Oct. 3, 2013, provisional application No. 62/192,406, filed on Jul. 14, 2015.

(51) Int. Cl.
  *A61K 35/742* (2015.01)
  *A61K 9/19* (2006.01)

(56) References Cited

OTHER PUBLICATIONS

Geuking, Markus B; et al; "Intestinal Bacterial Colonization Induces Mutualistic Regulatory T Cell Responses" Immunity, 34, 794-806, 2011.*
Overstreet, Anne-Marie Caroline; "Impact of antibiotic use, alternative therapies and inflammation on the intestinal microbiota" Graduate Theses and Dissertations, Iowa State University, 2012.*
Persky, Seth E; Brandt, Lawrence J; "Treatment of Recurrent Clostridium difficile—Associated Diarrhea by Administration of Donated Stool Directly Through a Colonoscope" The American Journal of Gastroenterology, 95, 3283-3285, 2000.*
GoLytely Product Sheet, Braintree Laboratories.*
Arya, Rvindra; et al; "Management of hepatic encephalopathy in children" Postgraduate Medical Journal, 86, 34-41, 2010.*
Aiba, Yuji et al., "Lactic Acid-Mediated Suppression of Helicobacter pylori by the Oral Administration of Lactobacillus salivarius as a Probiotic in a Gnotobiotic Murine Model", The American Journal of Gastroenterology, 93(11): 2097-2101 (1998).
Bartholomew, D. et al., "Prospective Diagnosis and Treatment of Urea Cycle Disorders", Pediatric Research, 21(4): Pediatric Research, 21(4), Part 2, p. 288A (1987) [Abstract only].
Ge, Zhongming et al., "Helicobacter hepaticus urease is not required for intestinal colonization but promotes hepatic inflammation in male A/JCr mice", Microbial Pathogenesis, 45: 18-24 (2008).
Hill, M.J. et al., "The normal colonic bacterial flora", Gut, 16(4): 318-323 (1975).
Kotani, Yasushi et al., "Carbamyl phosphate synthetase deficiency and postpartum hyperammonemia", American Journal of Obstetrics & Gynecology, 203(1): e10-e11 (2010).
Malin, M. et al., "Increased Bacterial Urease Activity in Faeces in Juvenile Chronic Arthritis: Evidence of Altered Intestinal Microflora?", British Journal of Rheumatology, 35: 689-694 (1996).
Wen, Li et al., "Innate immunity and intestinal microbiota in the development of Type 1 diabetes", Nature, 455(7216): 1109-1113 (2008).
Wong, L.T.K. et al., "Monitoring the Efficacy of Dietary Treatment in Urea Cycle Disorders", Journal of Inherited Metabolic Disease, 23, p. 50 (2000).
Extended European Search Report, dated May 12, 2017, issued in corresponding European Patent Application No. 14851064.7.
Mobley et al., "Microbial ureases: significance, regulation, and molecular characterization", Microbiol. Rev., 53: 85-108 (1989).
Bartosch et al., "Characterization of bacterial communities in feces from healthy elderly volunteers and hospitalized elderly patients by using real-time PCR and effects of antibiotic treatment on the fecal microbiota", Appl. Environ. Microbiol., 70: 3575-3581 (2004).
Wong et al., "Viabilty of Bifidobacterium Pseudocatenulatum G4 after Spray-Drying and Freeze-Drying", Microbiology Insights, 3: 37-43 (2010).
Arumugam, M. et al., "Enterotypes of the human gut microbiome", Nature, 473: 174-180 (2011).
Atarashi, K. et al., "Treg induction by a rationally selected mixture of Clostridia strains from the human microbiota", Nature, 500: 232-236 (2013).
Atarashi, K. et al., "Induction of Colonic Regulatory T Cells by Indigenous Clostridium Species", Science, 331: 337-341 (2011).
Bergersen, F.J. et al., "The Presence of N2-fixing Bacteria in the Intestines of Man and Animals", J. Gen. Microbiol, 60: 61-65 (1970).
Brown, D. et al., "Nitrogen stress response and stringent response are coupled in *Escherichia coli*", Nat. Commun., 5: 4115 doi: 10.1038/ncomms5115 (2014).
Frank, D. N. et al., "Molecular-phylogenetic characterization of microbial community imbalances in human inflammatory bowel diseases", pnas, 104(34) 13780-13785 (2007).
Garrett, W.S. et al., "Enterobacteriaceae Act in Concert with the Gut Microbiota to Induce Spontaneous and Maternally Transmitted Colitis", Cell Host & Microbe, 8: 292-300 (2010).
Hernandez, J. A. et al., "Molybenum Trafficking for Nitrogen Fixation", Biochemistry, 48: 9711-9721 (2009).
Iobbi-Nivol, C. et al., "Molybdenum enzymes, their maturation and molybdenum cofactor biosynthesis in *Escherichia coli*", Biochimica et Biophysica Acta, 1827: 1086-1101 (2013).
Lasaro, M. et al., "*Escherichia coli* Isolate for Studying Colonization of the Mouse Intestine and Its Application to Two-Component Signaling Knockouts", Journal of Bacteriology, 196(9): 1723-1732 (2014).
Leimkuhler, S., "The Biosynthesis of the Molybdenum Cofactor in *Escherichia coli* and Its Connection to FeS Cluster Assembly and the Thiolation of tRNA", Advances in Biology, Hindawi Publishing Corporation, vol. 2014.
Monnet, C. et al., "Selection and Properties of *Streptococcus thermophilus* Mutants Deficient in Urease", J. Dairy Sci., 87: 1634-1640 (2004).
Mora, D. et al., "Genetic diversity and technological properties of *Streptococcus thermophilus* strains isolated from dairy products", Journal of Applied Microbiology, 93: 278-287 (2002).
Moreno-Vivian, C. et al., "Prokaryotic Nitrate Reduction: Molecular Properties and Functional Distinction among Bacterial Nitrate Reductases", Journal of Bacteriology, 181(21): 6573-6584 (1999).
Qin, N. et al., "Alterations of the human gut microbiome in liver cirrhosis", Nature, 513: 59-63 (2014).
Reitzer, L. et al., "Nitrogen Assimilation and Global Regulation in *Escherichia coli*", Annu. Rev. Microbiol., 57: 155-76 (2003).
Sartor, R. et al., "Microbial Influences in Inflammatory Bowel Diseases", Gastroenterology, 134: 577-594 (2008).
Schabi, B. et al., "Interactions Between the Intestinal MIcrobiome and Liver Diseases", Gastroenterology, 146: 1513-1524 (2014).
Shen, T.-C. et al., "Engineering the gut microbiota to treat hyperammonemia", The Journal of Clinical Investigation, 125(7): 2841-2850 (2015).
Winter, S.E. et al., "Host-Derived Nitrate Boosts Growth of *E-coli* in the Inflamed Gut", Science, 339: 708-711 (2013).

* cited by examiner

Clustering ASF 16S rRNA gene tags

Assessing Urease Function of the ASF Community
Fecal Urease Test
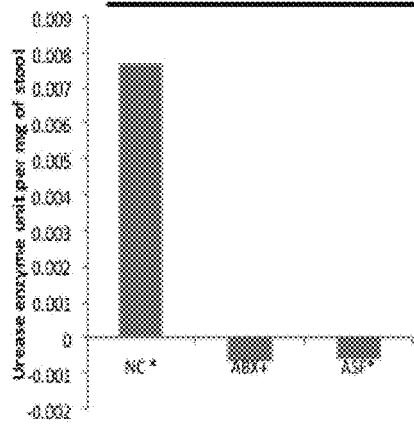
Figure 5B
Ammonia assay
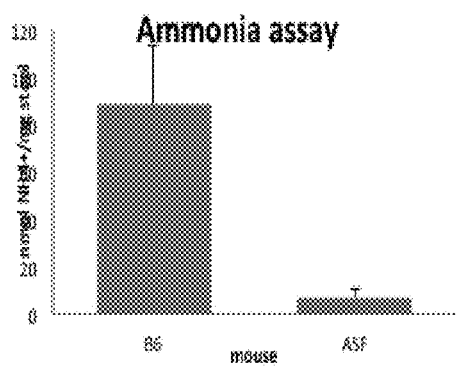
Figure 5C
Urease Breath Test
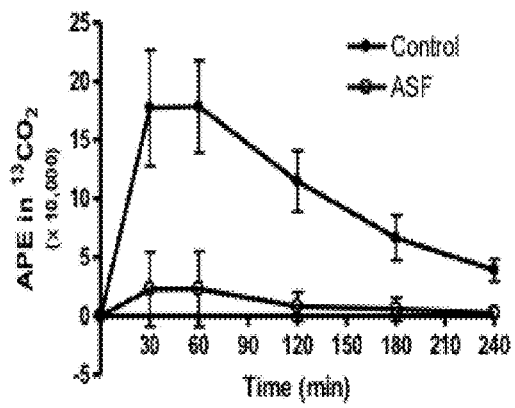
Label ($^{13}CO_2$) in Breath After $^{13}C$-Urea
(Controls vs. ASF Inoculated Mice)
*(Data normalized to $^{13}C$-Urea Label)*
Figure 5D

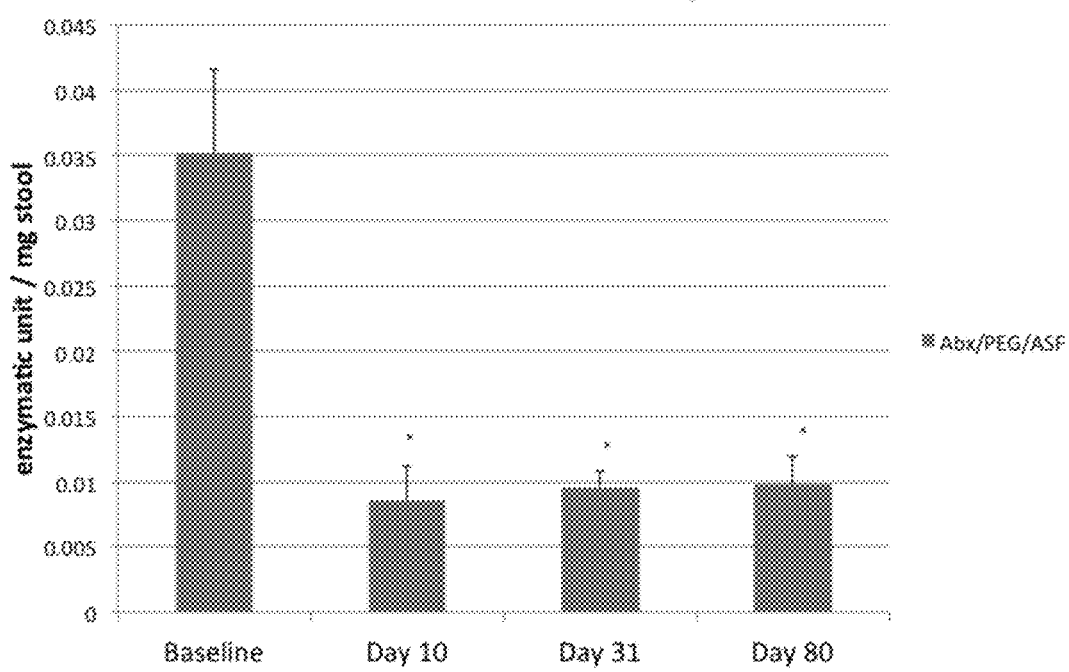

Ammonia results for Lillian/Mike's samples continued

Average NH4+ in stool from Abx/PEG/ASF treated mice on normal chow in JM3

ASF fecal amino acid analysis

ASF Fecal SCFA Analysis

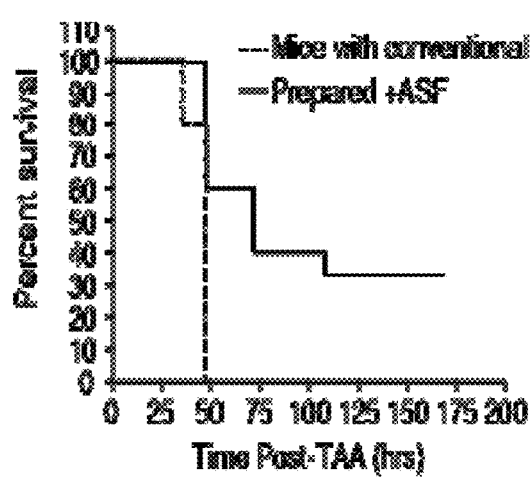 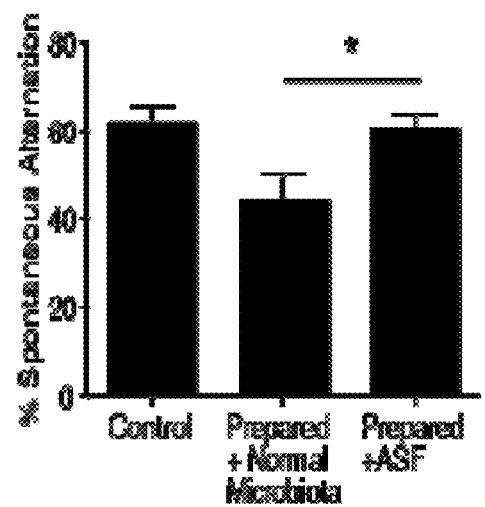
Figure 10A                    Figure 10B

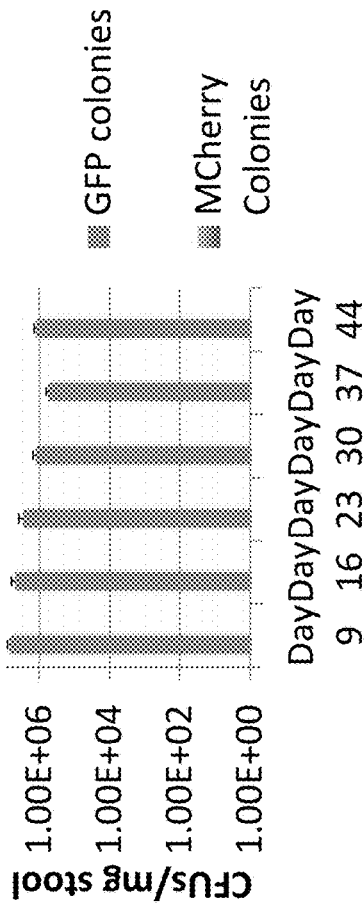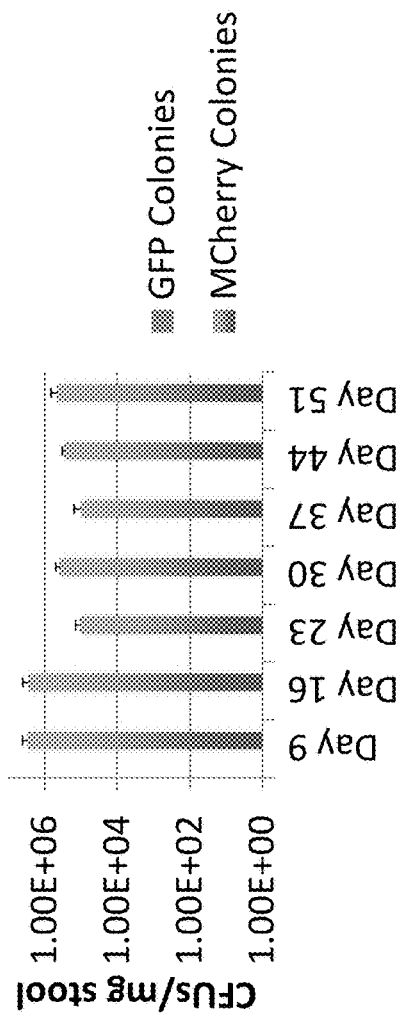
Fig. 16

Fig. 17 Differential reconfiguration of the gut microbiota using a single organism (E. coli, a facultative anaerobe) with, or lacking, a urease gene

COMPOSITIONS AND METHODS COMPRISING A DEFINED MICROBIOME AND METHODS OF USE THEREOF

PRIORITY CLAIM

This application is a continuation in part application of PCT/US2014/059166 filed Oct. 3, 2014 which claims priority to U.S. Provisional Application Nos. 61/886,268 and 61/974,686 filed Oct. 3, 2013 and Apr. 3, 2014 respectively. This application also claims priority to U.S. Provisional Application No. 62/192,406 filed Jul. 14, 2015. Each of these applications is incorporated herein by reference as though set forth in full.

STATEMENT OF RIGHTS TO INVENTIONS MADE UNDER FEDERALLY SPONSORED RESEARCH

This work was supported by the following grants from the National Institutes of Health, Grant Nos: UH2/3 DK083981 and DK089472. The government has certain rights in the invention.

BACKGROUND OF THE INVENTION

Growing evidence implicates the gut microbiome as a factor in the pathogenesis of a number of disease processes, including inflammatory bowel diseases, atherosclerosis, obesity, diabetes, and colon cancer. The association of these disease processes with an altered microbial community structure suggests that interventions that restore the normal resilient gut microbial community might be an innovative intervention for the treatment of *Clostridium difficile* colitis, hyperammonemia associated with inborn errors of metabolism, and inflammatory bowel disease.

Hyperammonemia occurs in many inherited metabolic diseases, most prominently in urea cycle disorders, where there is a failure to detoxify ammonia to urea. Current treatment includes a low-protein diet and drugs that relieve hyperammonemia, but these approaches are only partially effective in preventing/treating the devastating neurologic consequences caused by elevated levels of circulating ammonia. A significant amount of body ammonia forms in the gut from the hydrolysis of urea by intestinal bacteria. Oral antibiotic treatment may attenuate hyperammonemia, but the effectiveness of antibiotics wanes over time due to the development of antibiotic resistance.

There is a need in the art for novel methods of treating a subject having a disease associated with an undesirable gut microbiome. There is a further need in the art for novel methods of restoring normal gut flora in a subject or altering the gut microbiota associated with disease to alleviate symptoms caused by the disease. The present invention addresses these needs.

SUMMARY OF THE INVENTION

In accordance with the present invention, a method for altering gut microbiota in a subject to reduce urease gene content or activity via reducing or eliminating urease producing bacteria from the gut in order to reduce ammonia production therefrom is disclosed. An exemplary method comprises administering a composition comprising a defined microbial consortia of bacteria to the subject, the bacteria having minimal urease activity or no urease gene content, under conditions wherein the bacteria colonize the gut. The method results in the beneficial reduction of urease gene content, or activity or both in gut microbiota and ammonia production in the gut of the subject. In certain embodiments of the invention, the subject is treated with an effective amount of one or more antibiotics sufficient to reduce the population of bacteria in the gut microbiota to a level suitable for repopulation of newly introduced bacteria. The subject may also optionally be administered an effective amount of a purgative agent, thereby purging the intestines of said subject, prior to administration of the inventive microbial consortia of the invention. In another embodiment, the subject is treated with both antibiotics and a purging agent.

In certain embodiments, the subject has a disease associated with an undesirable gut microbiome, said treatment alleviating symptoms associated with said undesirable gut microbiome. The composition can be administered to the subject via several routes, which include, without limitation, endoscopy, by enteroscopy, by colonoscopy, a nasoduodenal catheter, an enema and orally in a consumable capsule or pill.

In one embodiment, the defined microbial consortia comprises one or more bacteria belonging to a genus selected from the group consisting of *Bifidobacterium, Bacteroides, Tannerella, Parabacteroides, Bacillus, Lactobacillus, Anaerostipes, Anaerostipes, Blautia, Coprococcus, Dorea, Clostridium XI, Collinsella*, and *Paraprevotella*. In a preferred embodiment, the consortia comprises *Clostridium* sp., *Lactobacillus* sp., *Lactobacillus murinus, Mucispirillum schaedleri, Eubacterium plexicaudatum, Firmicutes bacterium, Clostridium* sp. and *Parabacteroides* sp. In a particularly preferred embodiment, the consortia consists of *Paraprevotella clara, Bifidobacterium longum, Collinsella aerofaciens, Coprococcus comes, Dorea longicatena, Bacteroides eggerthii str.*, and *Bacteroides vulgates*.

The method of the invention can be used to advantage for the treatment of a variety of disorders, which include, without limitation, Carbamyl phosphate synthetase deficiency, Ornithine transcarbamylase deficiency, Arginosuccinate synthetase deficiency, Arginosuccinate lyase deficiency, Arginase deficiency, or N-acetylglutamate synthetase deficiency, Propionic acidemia, Methylmalonic acidemia, Isovaleric acidemia, Fatty Acid Oxidation Disorder, Short chain acyl-coA dehydrogenase deficiency, Medium-chain acyl-coA dehydrogenase deficiency, Long-chain acyl-coA dehydrogenase deficiency, a disorder of Amino Acid Transport, Lysinuric protein intolerance, Hyperammonemia, hyperornithinemia, homocitrullinemia syndrome, Transient Hyperammonemia of the Newborn, hyperinsulinemia, hypoglycemia syndrome, *Clostridium difficile* colitis, inflammatory bowel disease, atherosclerosis, obesity, metabolic syndrome, diabetes, colon cancer, cirrhosis, and hepatic encephalopathy.

In another embodiment, the method comprises determining the efficacy of treatment by assessing a parameter selected from the group consisting of 16S rRNA copy number, 16S rRNA gene sequencing, fecal urease levels, fecal or circulating amino acids, biogenic amines, fecal ammonia levels, and circulating ammonia levels.

In yet another aspect, a composition comprising an effective amount of a defined microbial consortia is provided. An exemplary consortia comprises a combination of one or more bacteria selected from the group consisting of *Bifidobacterium, Collinsella, Bacteroides, Petrimonas, Tannerella, Parabacteroides, Bacillus, Isobaculum, Enterococcus, Lactobacillus, Anaerostipes, Blautia, Coprococcus, Dorea, Oribacterium, Syntrophococcus, Clostridium XI,*

*Catenibacterium, Mitsuokella, Escherichia/Shigella,* and *Paraprevotella,* said consortia being effective to reduce urease levels in gut microbiota, said composition being present in a biological carrier suitable for administration to, and colonization of the gut. In yet another embodiment, the consortia consists of bacteria belonging to a genus selected from the group consisting of *Bifidobacterium, Bacteroides, Tannerella, Parabacteroides, Bacillus, Lactobacillus, Anaerostipes, Anaerostipes, Blautia, Coprococcus, Dorea,* and *Clostridium XI.* In a particularly preferred embodiment, the consortia comprises at least *Paraprevotella clara, Bifidobacterium longum, Collinsella aerofaciens, Coprococcus comes, Dorea longicatena, Bacteroides eggerthii str.,* and *Bacteroides vulgates.*

Also encompassed by the present invention is a process for preparing a defined microbial consortia composition for decreasing urease levels in the gut. The process comprising preparing a liquid culture of bacteria cells comprising said defined microbial consortia described above, harvesting the cells after a suitable period of growth and resuspending the cells in lyophilization medium, the medium optionally comprising cyroprotectorants, and, biological or chemical oxygen scavengers. The cells are then transferred into a lyophilizer under anaerobic conditions and lyophilized. Lyophilized cells are then packaged into a capsule or pill under oxygen free conditions and optionally further packaged into glass ampoules to maintain anaerobic conditions during shipment and storage. Also provide are capsules or pills containing the defined microbial consortia produced by the foregoing process.

In yet another aspect of the invention, the method entails administration of a single urease negative bacterial population for altering gut microbiota to reduce urease gene content or activity. The steps employed for this approach are comparable to those provided above. In this embodiment, the bacteria are selected from the group consisting of urease negative *Lactobacillus acidophilus L. acidophilus, L. acidophilus, L. acidophilus, Lactobacillus casei, L. casei Immunitas, Lactobacillus fermentum, Lactobacillus johnsonii, Lactobacillus paracasei Lactobacillus plantarum, Lactobacillus reuteri, Lactobacillus rhamnosus, Lactobacillus salivarius, Lactobacillus lactis, Bifidobacterium lactis, Bifidobacterium longum,* and *Bifidobactenium breve.*

Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "a defined microbial consortia" is meant a purified and/or isolated population of known microbes.

By "undesirable gut microbiome" is meant a community of microbes comprising a pathogen or having a biological activity associated with a pathogenic process. In one embodiment, an undesirable gut microbiome comprises microbes having urease activity. In another embodiment, an undesirable gut microbiome comprises an increased number or percentage of *Clostridium difficile* relative to the number or percentage of *C. difficile* and/or toxin production present in the gut of a healthy control subject.

By "normal gut microbiota" is meant a population of microbes that is substantially similar to the population of microbes present in the gut of a healthy control subject.

By "ameliorate" is meant decrease, suppress, attenuate, diminish, arrest, or stabilize the development or progression of a disease.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ. Exemplary diseases include hyperammonemia, *Clostridium difficile* colitis, hepatic encephalopathy associated with cirrhosis, and inflammatory bowel disease.

By "effective amount" is meant the amount of a composition of the invention (e.g., defined microbial consortia) required to ameliorate the symptoms of a disease relative to an untreated patient. The effective amount of a defined microbial consortia varies depending upon the manner of administration, the indication for administration, the age, body weight and height, sex, and general health of the subject. Ultimately, the attending physician or veterinarian will decide the appropriate amount and dosage regimen. Such amount is referred to as an "effective" amount.

The terms "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. Thus, a purified isolated bacterium that is part of a defined microbial consortia is at least about 90%, 95% or 100% free of bacteria, fungi, viruses, or other undefined microbes.

By "marker" is meant any analyte associated with a disease or disorder. In one embodiment, a marker of the invention is urease activity (e.g., fecal urease) or circulating ammonia.

By "reference" is meant a standard or control condition.

By "subject" is meant a mammal, including, but not limited to, a human or non-human mammal, such as a bovine, equine, canine, ovine, or feline.

By "instructional materials" is meant any information, resource and guidance that helps teaching and transferring skills to others.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a graph showing 16S copy number in ASF bacteria relative to a conventional microbiota. FIG. 1B shows results of a UniFrac-based PCoA analysis. FIG. 1C shows results of 16S rRNA sequencing of sequential fecal pellets collected from ten mice.

FIG. 2A and FIG. 2B are graphs. FIG. 2A shows that 16S rRNA copy number is reduced by approximately 4 logs 72 hours following oral antibiotic initiation. 16S rRNA copy number returns to baseline 5 days after discontinuing antibiotics (FIG. 2A). FIG. 2B shows that 16S copy number was restored to baseline levels after ASF transplantation. FIG. 2C shows that ASF transfer was as effective in pre-treated conventionally housed as germ-free recipients.

FIGS. 5A-5D relate to the presence of a urease gene and urease activity in ASF. FIG. 5A show results of ASF genomic sequencing. FIG. 5B and FIG. 5D show results of urease assays in feces and using breath testing. FIG. 5C shows results of an ammonia assay.

FIG. 6 shows results of a fecal urease activity analysis.

(FIG. 9A) Post ASF transplant fecal ammonia levels in the high dose TAA study shown in FIG. 11. (FIG. 9B) Kaplan-Meier survival curves and (FIG. 9C) fecal ammonia levels in the low dose TAA study associated with results shown in FIG. 5 (NF FMT=Normal flora fecal microbiota transplant. (FIG. 9D) Photomicrographs of H&E stained hepatic sections from mice treated with high dose TAA as indicated (200×) with quantification of hepatocellular necrosis (FIG. 11*b*).

FIGS. 10A and 10B show ASF transplantation into prepared mice reduces mortality and neurobehavioural abnormalities after thioacetamide-induced hepatic injury. (FIG. 10A) Kaplan-Meier survival curves of high dose TAA-induced hepatic injury in conventional vs. Prepared mice transplanted with ASF (N=15). (FIG. 10B) Spontaneous alternations quantified by Y-maze testing in Prepared mice that have received a fecal microbiota transplant (FMT) of either normal feces (NF) or ASF before TAA-induced hepatic injury (N=11 in ASF, N=10 in NF, N=5 in control, *p<0.05).

(FIG. 11A) Plasma alanine amino transferase (ALT) levels in untransplanted, antibiotic-treated, or ASF transplanted mice after TAA induced hepatic injury (N=10 in untransplanted and ASF transplanted groups, N=5 in control and antibiotic treated groups). (FIG. 11B) Liver damage quantified histologically by a pathologist reported as percent hepatic cellular necrosis (N=5 in each group, 10 random 200× HPF per liver, no statistically significant difference amongst the three treatment groups; blinded analysis).

FIG. 16 shows durable engraftment of *E. coli* MP-1 in a prepared host at levels 3 logs greater than previously described in the literature. The *E. Coli* MP-1 strain of bacteria, a normal commensal organism in the murine gut was engineered to express the *Proteus* urease gene (wild-type condition is urease negative). After preparing the murine host with vanco/neo and PEG, inoculation of mice with either the URE+ or URE− strains of MP-1 led to high level engraftment of *E. coli* ($10^6$) which is 3 logs greater than previously described in the literature. CFU=colony forming units, URE+MP-1 tagged with GFP, URE− MP-1 tagged with Tomato Red.

FIG. 15). There was also no significant alteration in the composition of the gut microbiota based on 16S rRNA gene sequencing. FIG. 22A. These results show the importance of bowel lavage in the depletion of gut bacteria. Bacterial load, represented by 16S gene copy number, in stool samples obtained from healthy adults who were treated with vancomycin, neomycin, and a bowel lavage with polyethylene glycol (PEG). The samples obtained at baseline, during antibiotic therapy but before the lavage, and after antibiotic therapy plus lavage suggest that the lavage is effective to more significantly deplete gut bacteria in humans. FIG. 22B is graph showing that cultured human gut microbiota can be reduced by over 5 logs (100,000-fold) similar to what we achieve in mice[10] using a combination of Neomycin, Vancomycin, and PEG to prepare the host for inoculation. The difference between the reduction in 16S copy number determined by qPCR likely represents the detected of DNA from dead bacterial after antibiotic treatment.

DETAILED DESCRIPTION OF THE INVENTION

Figure 1A:
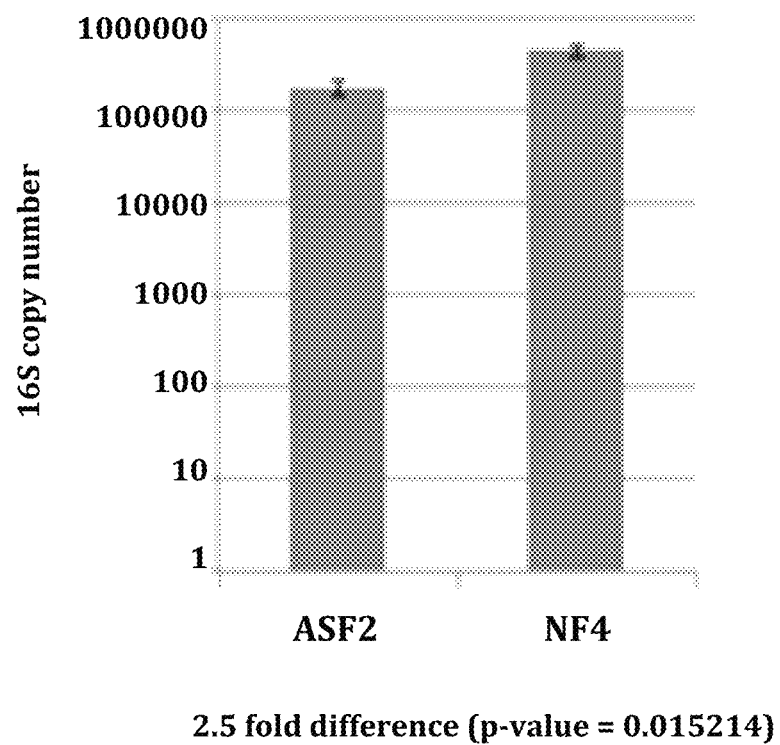
FIGS. 1A-1C show that there the abundance of bacteria is relatively similar between ASF and the normal commensal microbiota (NF4). Nevertheless ASF composition is distinctive from the commensal microbiota in a 16S rRNA PCoA plot (FIG. 1B, red=ASF, blue=conventional). The ASF consortium shows significant resilience when ASF colonized mice are housed in a SPF environment for approximately 1 month.

The invention features use of a defined microbial consortia for the replacement of a gut microbiome associated with disease.

The invention is based, at least in part, on the discovery that transplantation of a defined microbial consortia into a subject provides for the long term replacement of a gut microbiome associated with disease. While fecal transplantation has been used to treat subjects with diseases associated with undesirable changes in the gut microbiome, inoculating subjects with undefined complex microbial communities raise a number of safety concerns. In particular, the possibility that fecal transplant might inadvertently result in the transfer of pathogens into a susceptible host. Therefore, a need exists to identify defined microbial consortia with well characterized biological functions that can be used to target gut microbiome-associated diseases.

As reported herein below, Altered Schaedler's Flora (ASF), a defined consortia of eight bacteria, were transferred into previously colonized mice where the flora remained a robust and resilient community for at least four months under specific pathogen free (SPF) housing conditions.

Functional resiliency of the ASF community was demonstrated by genomic sequencing along with biochemical analyses that revealed the sustained lack of fecal urease activity and ammonia production in ASF transplanted mice. Unexpectedly, metabolomic analyses revealed the ASF transplanted mice were deficient in essential amino acids, a consequence of reduced microbial amino acid synthesis due to a deficiency in urease dependent ammonia production and the resultant inability of these mice to obtain dietary essential amino acids through corprophagia. These results demonstrate important syntrophic interactions between the host and the gut microbiome that may be of fundamental importance in the development of defined microbial communities for the treatment of disease.

Bacteria residing in the human gut produce urease, the activity of which is beneficial in healthy hosts but pathogenic in hosts with liver disease and other disorders. Urea produced by the liver as a waste product is both excreted in urine and transported into the colon, where it is hydrolyzed by bacterial urease into carbon dioxide and ammonia. Ammonia is then 1) utilized by the microbiota for amino acid, protein, and other small molecule syntheses via nitrogen flux, 2) reabsorbed by the host where it is incorporated into the nitrogen pool by hepatic metabolism, or 3) excreted in the feces. Mammalian genomes do not encode urease genes, so ammonia production results from bacterial urease activity acting on host-produced urea. Ammonia is also largely responsible for the alkaline pH of the colonic luminal environment, acting to buffer the short chain fatty acids also produced by the microbiota.

From the standpoint of the host, systemic ammonia levels are elevated in patients with liver injury, chronic liver disease or urea cycle defects, where hepatic abnormalities prevent the normal processing of ammonia delivered to the liver from the intestinal tract. Circulating ammonia is correlated with damage to the central nervous system in patients with chronic liver disease or inborn errors of metabolism, resulting in hepatic encephalopathy (HE).

Thus, in another aspect of the invention, methods for altering the gut microbiota via introduction of a single species of facultative anaerobic or aerobic urease negative bacteria, optionally following a gut purging treatment, are disclosed. The present inventors have found that such treatment provides therapeutic benefit to patients suffering from various disease states, particularly IBD.

Dysbiosis and Disease

Growing evidence implicates the gut microbiome as a factor in the pathogenesis of a number of diseases. The association of certain disease processes with alterations in the gut microbiome suggests that interventions that restore the normal resilient gut microbial community or alter the gut microbiota to remove undesirable bacteria should provide an innovative intervention for disease treatment. Indeed, the high level of efficacy of fecal microbiota transplantation (FMT) in the treatment of refractory *Clostridia difficile* infection (CDI) provides proof-of-principle that a specific human disease can be treated by inoculation with a gut microbial community. Together with studies in animal models (antibiotics in the development of *C. difficile* and *Salmonella*), these results also reinforce that notion that the use of a resilient microbial community is important to prevent and/or treat disease. Indeed, current probiotics consisting of a single or few live bacterial strains are largely ineffective in the treatment of *Clostridia difficile* infection.

Ultimately, fecal microbiota transplantation (FMT) will be replaced by the use of laboratory generated resilient microbial consortia that can be used to target specific diseases based on well-characterized microbial biological properties. One such example is the deleterious effects of ammonia production by the gut microbiota on the central nervous system in patients with chronic liver disease and/or inborn errors of metabolism, an entity known as hepatic encephalopathy. Treatments for hepatic encephalopathy include strategies to reduce microbial production of ammonia and its absorption. Therefore, the development of a resilient microbial community with minimal urease gene content to prevent or inhibit the production of ammonia should reduce the development of hepatic encephalopathy when inoculated into a susceptible patient population. When eliminating urease activity of the gut microbiota, it's important to recognize that the recycling of nitrogen through the production of ammonia is an example of symbiosis between the mammalian host and its gut microbiota that involves a syntrophic interaction (or cross-feeding). Urea production by the liver as a waste product is not only excreted in urine but is also transported into the colon where it is hydrolyzed by bacterial urease into both carbon dioxide and ammonia. Ammonia is then utilized by the microbiota for protein synthesis, reabsorbed by the host where it is reincorporated into the host nitrogen pool by hepatic metabolism, or excreted in the feces.

Using Altered Schaedler's Flora (ASF), a model gut microbial community that exhibits long term reduction in urease activity and ammonia production, along with both taxonomic and functional resiliency upon transplantation, was examined in a previously colonized host. The impact of ASF on host metabolism was also determined. Transplantation of ASF was highly efficient in the properly prepared host where it demonstrates a remarkable level of taxonomic resiliency over a period of 4 months under SPF housing conditions. Invasion of non-ASF taxa over time involved specific bacterial taxa of the *Fimicutes* phylum but not *Bacteroidetes*. Functionally, urease activity remained very low with minimal ammonia production over this same time period. ASF has been used for decades to colonize immune deficient mice without evidence of deleterious effects. Nevertheless, metabolic profiling of both the host and the transplanted microbiota revealed a reduction in essential amino acids demonstrating the importance of microbial urease activity in maintenance of the syntrophic interaction between the gut microbiome and its host with respect to nitrogen balance.

Methods of the Invention

The present invention provides methods of treating diseases or symptoms thereof associated with the presence of one or more undesirable bacteria in the gut of a subject. Accordingly, the invention provides compositions and methods for treating a subject having, or at risk of developing a disease associated with undesirable changes in the gut microbiome, the method involving administering a therapeutically effective amount of a composition comprising a defined microbial consortia, or single bacteria to a subject (e.g., a mammal, such as a mouse or human). Thus, one embodiment is a method of treating a subject suffering from or susceptible to a metabolic disease (e.g., an inborn error of metabolism, such as urea carbamylase deficiency).

In particular embodiments, the subject is identified as having a Urea Cycle Defect (e.g., Carbamyl phosphate synthetase deficiency, Ornithine transcarbamylase deficiency, Arginosuccinate synthetase deficiency, Arginosuccinate lyase deficiency, Arginase deficiency, or N-acetylglutamate synthetase deficiency. In other embodiments, the subject has an Organic Acidemias (e.g., Propionic acidemia, Methylmalonic acidemia, Isovaleric acidemia). In still other embodiments, the subject has a Fatty Acid Oxidation Disorder (e.g., Short chain acyl-coA dehydrogenase deficiency, Medium-chain acyl-coA dehydrogenase deficiency, Long-chain acyl-coA dehydrogenase deficiency) or a disorder of Amino Acid Transport (e.g., Lysinuric protein intolerance, Hyperammonemia, hyperornithinemia, homocitrullinemia syndrome). In still other embodiments, the subject has Transient Hyperammonemia of the Newborn, Hyperammonemia, hyperinsulinemi, or hypoglycemia syndrome.

In still other embodiments, the subject has cirrhosis, hepatic encephalopathy, or another liver disorder characterized by hyperammonemia. The method includes the step of administering to the mammal a therapeutic amount of an amount of a composition comprising a defined microbial consortia (e.g., a community of microbes deficient in urease activity) or single urease negative bacteria, sufficient to treat the disease or disorder or symptom thereof, under conditions such that the disease or disorder is treated.

In still other embodiments, the subject has *Clostridium difficile* colitis or inflammatory bowel disease.

Compositions comprising a defined microbial consortia preferably contain a combination of one or more (e.g., 1, 2, 3, 4, 5, 6, 7, 8, 9, 10, 15, 20, 25, 30, 35, 40, 45, 50) bacterial strains listed in Tables 1, 2, or 3A, 3B, 3C, 7A or 7B.

TABLE 1

Bacterial Strains from the Guts of Healthy Humans

| Phylum | Class | Order | Family | Genus |
|---|---|---|---|---|
| Actinobacteria | Actinobacteria | Bifidobacteriales | Bifidobacteriaceae | *Bifidobacterium* |
| Actinobacteria | Actinobacteria | Coriobacteriales | Coriobacteriaceae | *Collinsella* |
| Bacteroidetes | Bacteroidia | Bacteroidales | Bacteroidaceae | *Bacteroides* |
| Bacteroidetes | Bacteroidia | Bacteroidales | Porphyromonadaceae | *Petrimonas* |
| Bacteroidetes | Bacteroidia | Bacteroidales | Porphyromonadaceae | *Tannerella* |
| Bacteroidetes | Bacteroidia | Bacteroidales | Porphyromonadaceae | *Parabacteroides* |
| Firmicutes | Bacilli | Bacillales | Bacillaceae | *Bacillus* |
| Firmicutes | Bacilli | Lactobacillales | Carnobacteriaceae | *Isobaculum* |
| Firmicutes | Bacilli | Lactobacillales | Enterocaccaceae | *Enterococcus* |
| Firmicutes | Bacilli | Lactobacillales | Lactobacillaceae | *Lactobacillus* |
| Firmicutes | Clostridia | Clostridiales | Lachnospiraceae | *Anaerostipes* |
| Firmicutes | Clostridia | Clostridiales | Lachnospiraceae | *Blautia* |
| Firmicutes | Clostridia | Clostridiales | Lachnospiraceae | *Coprococcus* |
| Firmicutes | Clostridia | Clostridiales | Lachnospiraceae | *Dorea* |
| Firmicutes | Clostridia | Clostridiales | Lachnospiraceae | *Oribacterium* |
| Firmicutes | Clostridia | Clostridiales | Lachnospiraceae | *Syntrophococcus* |
| Firmicutes | Clostridia | Clostridiales | Peptostreptococcaceae | *Clostridium* XI |
| Firmicutes | Erysipelotrichia | Erysipelotrichales | Erysipelotrichaceae | *Catenibacterium* |
| Firmicutes | Negativicutes | Selenomonadales | Veillonellaceae | *Mitsuokella* |
| Proteobacteria | Gammaproteobacteria | Enterobacteriales | Enterobacteriaceae | *Escherichia/Shigella* |

TABLE 2

Microbiota Therapeutics Version 1 (MTv1)

| Phylum | Class | Order | Family | Genus | Reason for choice |
|---|---|---|---|---|---|
| Actinobacteria | Actinobacteria | Bifidobacteriaies | Bifidobacteriaceae | *Bacteroides* | common in healthy gut. populate the nodes, probiotic line acre |
| Actinobacteria | Actinobacteria | Coriobacteriales | Coriobacteriaceae | *Collinseiia* | |
| Bacteroidetes | Bacteroidia | Bacteroidales | Bacteroidaceae | *Bacteroides* | hASF, common in healthy gut populate the nodes |
| Bacteroidetes | Bacteroidia | Bacteroidales | Porphyromonadaceae | *Petrimortas* | |
| Bacteroidetes | Bacteroidia | Bacteroidales | Porphyromonadaceae | *Tannerella* | common in healthy gut, populate the nodes |
| Bacteroidetes | Bacteroidia | Bacteroidales | Porphyromonadaceae | *Parabacteroides* | hASF, common in healthy gut. populate the nodes |
| Firmicutes | Bacilli | Bacillales | Bacillaceae | *Bacillus* | common in healthy gut, populate the nodes |
| Firmicutes | Bacilli | Lactobacillales | Carnobacteriaceae | *isobaculum* | |
| Firmicutes | Bacilli | Lactobacillales | Enterocaccaceae | *Enterococcus* | |
| Firmicutes | Bacilli | Lactobacillales | Lactobacillaceae | *Lactobacillus* | hASF, common in healthy gut. populate the nodes, probiotic lineage |
| Firmicutes | Clostridia | Ciostridiales | Lachnospiraceae | *Anaerostipes* | common in healthy gut populate the nodes |
| Firmicutes | Clostridia | Clostridiales | Lachnospiraceae | *Blautia* | common in healthy gut, populate the nodes |
| Firmicutes | Clostridia | Ciostridiales | Lachnospiraceae | *Coprococcus* | common in healthy gut, populate the nodes |
| Firmicutes | Clostridia | Ciostridiales | Lachnospiraceae | *Dorea* | common in healthy gut, populate the nodes |
| Firmicutes | Clostridia | Clostridiales | Lachnospiraceae | *Oribacterium* | |
| Firmicutes | Clostridia | Clostridiales | Lachnospiraceae | *Syntrophococcus* | |

TABLE 2-continued

Microbiota Therapeutics Version 1 (MTv1)

| Phylum | Class | Order | Family | Genus | Reason for choice |
|---|---|---|---|---|---|
| Firmicutes | Clostridia | Clostridiales | Peptostreptococcaceae | *Clostridium XI* | hASF, common in healthy gut, populate the nodes |
| Firmicutes | Erysipelotricftia | Erysipelotrichales | Ervsipelotrichaceae | *Catenibacterium* | |
| Firmicutes | Neqativicutes | Selenomonadales | Veillonellaceae | *Mitsuokella* | |
| Proteobacteria | Gamma proteobacteria | Enterobacteriales | Enterobacteriaceae | *Escherichia/ Shigella* | |

*An exemplary defined microbial consortia comprises the bacteria shown in bold type.

TABLE 3A

Engineered human community low in urease

*Paraprevotella clara*
*Bifidobacterium longum*
*Collinsella aerofaciens*
*Coprococcus comes*
*Dorea longicatena*
*Bacteroides eggerthii* str.
*Bacteroides vulgatus*

TABLE 3B

Human orthologs of ASF

| | |
|---|---|
| *Clostridium* sp. | 356 |
| *Lactobacillus* sp. | 360 |
| *Lactobacillus murinus* | 361 |
| Flexistipes group | 457 |
| *Eubacterium plexicaudatum* | 492 |
| Low G--C content Gram + group | 500 |
| *Clostridium* sp. | 502 |
| *Bacteroides* sp. | 519 |

TABLE 3C

Mouse ASF species
Genome features and accession numbers of the ASF bacteria PMID: 24723722

| ASF no. | Taxonomy | Genome size (Mb) | GC (%) | Gene count | Contig count | $N_{50}$ (kb) | Fold cover-age | GenBank accession no. |
|---|---|---|---|---|---|---|---|---|
| ASF356 | *Clostridium* sp. | 2.91 | 30.91 | 2,799 | 31 | 209 | 143 | AQFQ00000000.1 |
| ASF360 | *Lactobacillus* sp. | 2.01 | 35.86 | 1,930 | 244 | 19 | 47 | AQFR00000000.1 |
| ASF361 | *Lactobacillus murinus* | 2.17 | 39.96 | 2,102 | 78 | 59.7 | 160 | AQFS00000000.1 |
| ASF457 | *Mucispirillum schaedleri* | 2.33 | 31.15 | 2,144 | 39 | 151 | 142 | AYGZ00000000.1 |
| ASF492 | *Eubacterium plexicaudatum* | 6.51 | 42.86 | 6,217 | 248 | 74.4 | 119 | AQFT00000000.1 |
| ASF500 | *Firmicutes* bacterium | 3.7 | 58.77 | 3,563 | 42 | 300 | 137 | AYJP00000000.1 |
| ASF502 | *Clostridium* sp. | 6.48 | 47.9 | 6,062 | 134 | 137 | 82 | AQFU00000000.1 |
| ASF519 | *Parabacteroides* sp. | 6.87 | 43.45 | 5,477 | 24 | 584 | 143 | AQFV00000000.1 |

The term "dysbiosis" refers to an alteration in the composition of the microbiota associated with disease. In obesity and metabolic syndrome, the dysbiotic microbiota is associated with a decrease in bacterial gene or taxonomic richness (lower number of different genes and/or bacterial taxa). However, in many diseases, such as liver disease (NASH and cirrhosis for example) and IBD, dysbiosis is also associated with an increase in bacteria belonging to the Proteobacteria phylum and a decrease in the *Firmicutes phylum*[1-3, 11, 12]. Proportionally, bacteria belonging to either the *Bacteroidetes* or *Firmicutes* phyla account for approximately 90% of the normal human gut microbiota with the remaining 10% being composed of primarily Actinobacteria and a smaller proportion of Proteobacteria[13]. The expansion of Proteobacteria in IBD-associated dysbiosis has been described to exceed 10% of the gut microbiota with a proportional decrease in *Firmicutes*[1]. Proving cause-and-effect relationships, enhancement of Proteobacteria exacerbate colitis[2] and *Firmicutes*, particularly *Clostridia*, reduce colitis in animal models[5].

Identifying a subject in need of treatment for a disease associated with the gut microbiome such as dysbiosis, can be in the judgment of a health care professional and can be subjective (e.g. opinion) or objective (e.g. measurable by a test or diagnostic method). As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of, or susceptible to, developing a disorder or condition.

The therapeutic methods of the invention (which include prophylactic treatment) in general comprise administration of a therapeutically effective amount of a composition comprising a defined microbial consortia to a subject (e.g., human) in need thereof. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider. The compositions herein may be also used in the treatment of any other disorders in dysbiosis may be implicated.

A subject is effectively treated whenever a clinically beneficial result ensues. This may mean, for example, a complete resolution of the symptoms associated with an undesirable gut microbiota, a decrease in the severity of the symptoms associated with an undesirable gut microbiota, or a slowing of the progression of symptoms associated with an undesirable gut microbiota. As described above, such symptoms can be the result of an inborn metabolic error, for example, a urease cycle deficiency; a liver injury or chronic liver disease. Regardless of the cause, such patients have an impaired ability to process the ammonia delivered to the liver from the intestinal tract. As a result, such patients suffer from high circulating ammonia levels (hyperammonemia) which are correlated with damage to the central nervous system and can result in hepatic encephalopathy.

Thus in general, the methods include administering a defined microbial consortia having reduced urease activity to a patient having an undesirable gut microbiota. These methods can further include the steps of a) identifying a subject (e.g., a patient and, more specifically, a human patient) who has an undesirable gut microbiota, and b) providing to the subject a composition comprising a defined microbial consortia described herein. An amount of such a composition provided to the subject that results in a complete resolution of the symptoms associated with an undesirable gut microbiota, a decrease in the severity of the symptoms associated with an undesirable gut microbiota, or a slowing of the progression of symptoms associated with an undesirable gut microbiota, is considered a therapeutically effective amount. The present methods may also include a monitoring step to help optimize dosing and scheduling as well as predict outcome.

The present methods can include the steps of administering a treatment to reduce the level of bacteria within the intestinal lumen of the subject prior to administering a composition comprising any of the defined microbial consortia described herein. Thus the subject, whom we may refer to as a recipient or a host, can be pretreated to reduce the level of endogenous bacteria prior to administration of compositions. Pretreatment regimens can include specific antimicrobial agents, for example one or more antibiotics, for example, rifaximin, metronidazole, trimethoprim-sulfamethoxazole, neomycin or vancomycin. Pretreatment regimens can include non-specific agents, for example, a purgative, for example, polyethylene glycol or a laxative, for example, bisacodyl. Pretreatment regimens can also include dietary modification. The pretreatment regimen can include a combination of any of the treatment modalities above, for example, administration of an antibiotic, a purgative, a laxative, along with dietary modification. Concurrent administration of two or more agents does not require that the agents be administered at the same time or by the same route, as long as there is an overlap in the time period during which the agents are exerting their therapeutic effect. Simultaneous or sequential administration is contemplated, as is administration on different days or weeks.

The compositions can also include a pharmaceutically acceptable carrier. We use the terms "pharmaceutically or biologically acceptable" (or "pharmacologically acceptable") to refer to molecular entities and compositions that do not produce an adverse, allergic or other untoward reaction when administered to an animal or a human, as appropriate. The term "pharmaceutically acceptable carrier," as used herein, includes any and all solvents, dispersion media, coatings, antibacterial, isotonic and absorption delaying agents, buffers, excipients, binders, lubricants, gels, surfactants and the like, that may be used as media for a pharmaceutically acceptable substance.

This methods of the invention include administration of a defined microbial consortia of bacteria having minimal urease activity formulated as pharmaceutical compositions which contain, as the active ingredient, the defined microbial consortia described herein, in combination with one or more pharmaceutically acceptable carriers. In some embodiments, the defined microbial consortia can be sterilized using conventional sterilization techniques before or after it is combined with the pharmaceutically acceptable carrier. In making the compositions of the invention, the defined microbial consortia are typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. As is known in the art, the type of diluent can vary depending upon the intended route of administration. The resulting compositions can include additional agents, such as preservatives. The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary). Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

Pharmaceutically acceptable compositions for use in the present methods, including those in a defined microbial consortium having minimal urease activity, can be entrapped in a colloid for oral delivery. Pharmaceutically acceptable compositions can be prepared according to standard techniques. The defined microbial consortium having minimal urease activity can be dried and compacted by grinding or pulverizing and inserted into a capsule for oral administration. In some embodiments, the defined microbial consortium having minimal urease activity can be combined one or more excipients, for example, a disintegrant, a filler, a glidant, or a preservative. Suitable capsules include hard shell capsules, or soft-shelled capsules. Any lipid-based or polymer-based colloid may be used to form the capusule. Exemplary polymers useful for colloid preparations include gelatin, plant polysaccharides or their derivatives such as carrageenans and modified forms of starch and cellulose, e.g., hypromellose. Optionally, other ingredients may be added to the gelling agent solution, for example plasticizers such as glycerin and/or sorbitol to decrease the capsule's hardness, coloring agents, preservatives, disintegrants, lubricants and surface treatment. In some embodiments, the capsule does not include gelatin. In other embodiments, the capsule does not include plant polysaccharides or their derivatives.

Regardless of their original source or the manner in which they are obtained, the compositions comprising the defined microbial consortium having minimal urease activity can be formulated in accordance with their use. These compositions can be prepared in a manner well known in the pharmaceutical art, and can be administered by a variety of routes, depending upon whether local or systemic treatment is desired and upon the area to be treated. Administration may be oral, gastrointestinal, or rectal. Administration can be in the form of a single bolus dose, or may be, for example, by a continuous perfusion pump.

The compositions can be formulated in a unit dosage form, each dosage containing, for example, from about 0.005 mg to about 2000 mg of a defined microbial consortium having minimal urease activity per dose. The phrase "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.005 mg to about 1000 mg of the defined microbial consortium having minimal urease activity of the present invention.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient.

In some embodiments, tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The proportion or concentration of the compositions of the invention in a pharmaceutical composition can vary depending upon a number of factors including dosage, chemical characteristics (e.g., hydrophobicity), and the route of administration. For example, the defined microbial consortium having minimal urease activity can be provided in a capsule containing from about 0.005 mg to about 1000 mg for oral administration. Alternatively or in addition, the dosage can be expressed as cfu/g of dry weight. The dosage may vary, but can range from the equivalent of about $10^2$ to about $10^{12}$ cfu/g, e.g., $1\times10^2$ cfu/g, $5\times10^2$ cfu/g, $1\times10^3$ cfu/g, $5\times10^3$ cfu/g, $1\times10^4$ cfu/g, $5\times104$ cfu/g, $1\times105$ cfu/g, $5\times10^5$ cfu/g, $1\times10^6$ cfu/g, $5\times10^6$ cfu/g, $1\times10^7$ cfu/g, $5\times10^7$ cfu/g, $1\times10^8$ cfu/g, $5\times10^8$ cfu/g, $1\times10^9$ cfu/g, $5\times10^9$ cfu/g, $1\times10^{10}$ cfu/g, $5\times10^{10}$ cfu/g, $1\times10^{11}$ cfu/g, $5\times10^{11}$ cfu/g, $1\times10^{12}$ cfu/g, of dry weight.

Compositions comprising a defined microbial consortia can be administered to the gastrointestinal tract of a subject by nasoduodenal catheter, by enema, or by endoscopy, enteroscopy, or colonoscopy or orally in a consumable capsule or pill. In certain embodiments, the defined microbial consortia are diluted in a suitable excipient (e.g., saline solution). In a preferred embodiment, the bacteria are delivered in lyophilized form.

Regardless of how the compositions are formulated, the dosage required will depend on the route of administration, the nature of the formulation, the nature of the subject's condition, e.g., immaturity of the immune system or a gastrointestinal disorder, the subject's size, weight, surface area, age, and sex, other drugs being administered, and the judgment of the attending clinicians. In some embodiments, suitable dosages are in the range of 0.01-1,000 mg/kg. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. Alternatively or in addition, the dosage can be expressed as cfu/g of dry weight. The dosage may vary, but can range from the equivalent of about $10^2$ to about $10^{12}$ cfu/g, e.g., $1\times10^2$ cfu/g, $5\times10^2$ cfu/g, $1\times10^3$ cfu/g, $5\times10^3$ cfu/g, $1\times10^4$ cfu/g, $5\times10^4$ cfu/g, $1\times10^5$ cfu/g, $5\times10^5$ cfu/g, $1\times10^6$ cfu/g, $5\times10^6$ cfu/g, $1\times10^7$ cfu/g, $5\times10^7$ cfu/g, $1\times10^8$ cfu/g, $5\times10^8$ cfu/g, $1\times10^9$ cfu/g, $5\times10^9$ cfu/g, $1\times10^{10}$ cfu/g, $5\times10^{10}$ cfu/g, $1\times10^{11}$ cfu/g, $5\times10^{11}$ cfu/g, $1\times10^{12}$ cfu/g of dry weight. Preferably, at least $1\times10^{10}$ cfu/g is used.

The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems. Useful assay systems include for example, analysis of the particular gut microbial community, fecal urease activity or ammonia levels. Wide variations in the needed dosage are to be expected in view of the variety of useful microbial consortia and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). The duration of treatment with any composition provided herein can be any length of time from as short as one day to as long as the life span of the host (e.g., many years). For example, a composition can be administered once a week (for, for example, 4 weeks to many months or years); once a month (for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

Any method known to those in the art can be used to determine if a particular response is induced. Clinical methods that can assess the degree of a particular disease state can be used to determine if a response is induced. For example, a subject can be monitored for symptomatic relief, e.g., relief from lethargy, irritability, poor feeding, vomiting hyperventilation, seizures, ataxia. Alternatively or in addition, serum markers, for example, plasma concentration of ammonium, arginine, citrulline; urinary markers, for example, orotic acid can also be assayed The compositions may also be administered in conjunction with other therapeutic modalities. Other therapeutic modalities will vary according to the particular disorder, but can include, for example, dietary modification, hemodialysis, therapeutic agents such as sodium benzoate, phenylacetate, arginine, or surgical remedies, for example, liver transplantation. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

In one embodiment, the invention provides a method of monitoring treatment progress, for example, by measuring urease activity (e.g., fecal urease), fecal ammonia levels or circulating ammonia levels. In other embodiments, the monitoring involves detecting gut microbes (e.g., by 16S rRNA gene sequencing or 16S rRNA copy number). The method includes the step of determining a level of diagnostic marker (marker) or diagnostic measurement (e.g., screen, assay) in a subject suffering from or susceptible to a disorder or symptoms thereof associated with dysbiosis, in which the subject has been administered a therapeutic amount of a composition herein sufficient to treat the disease or symptoms thereof. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to this invention; this pre-treatment level of marker can then be compared to the level of marker in the subject after the treatment commences, to determine the efficacy of the treatment. In certain preferred embodiments, a level of marker in the subject is determined serially after beginning treatment according to this invention; the level of marker can then be compared over time to determine the efficacy of the treatment and need for dose adjustment.

Formulation of Microbial Consortia, Single Bacteria Formulations, and Methods of Delivery Compositions comprising a defined microbial consortia or a single bacteria composition are preferably administered to a subject by nasoduodenal catheter, by enema, or by endoscopy, enteroscopy, or colonoscopy or orally in a consumable capsule or pill. In certain embodiments, the defined microbial consortia are diluted in a suitable excipient (e.g., saline solution). In a preferred embodiment, the bacteria are delivery in lyophilized form. An exemplary protocol for this approach is provided below to facilitate practice of the invention.

Lyophilization Procedure and Process Development:

In one aspect, the microbial consortium will be delivered as a lyophilized (freeze-dried) powder packaged in a consumable gelatin capsule. In brief, the liquid culture will be: centrifuged, resuspended in a lyophilization medium which will optionally include cryoprotectants and biological- and/ or chemical-oxygen scavengers (See Table 5) transferred under anaerobic conditions to a shelf lyophilizer, lyophilized, encapsulated in a gelatin capsule under anaerobic conditions, and packaged in a glass ampoule to maintain oxygen free conditions during transport and storage. Details on each of these steps, as well as method development and quality control (QC) considerations are detailed below.

Preparation of Culture for Lyophilization.

Liquid cultures ($10^{10}$ colony forming units, or CFU) of the strain(s) in the logarithmic or early stationary phase of growth are centrifuged to form a pellet of cells. The culture medium (supernatant) is then removed, and the pellet resuspended in a lyophilization medium; multiple lyophilization medium can be utilized and include without limitation, those set forth in Table 4.

TABLE 4

| Different lyophilization medium for formulation of the microbial consortium. Lyophilization Medium |
| --- |
| 10-20% (wt./vol) skim milk[1-3] Reagent 18 (Tryticase Soy Broth, Sucrose, Bovine Serum Albumin Fraction V)[1,2] Reagent 20 (Sucrose, Bovine Serum Albumin Fraction V)[1] Microbial Freeze Drying Buffer[2,3] |

Following lyophilization of the consortium, we will optionally include in the formulation oxygen-scavenging excipients for reducing $O_2$, thereby protecting the obligate anaerobic consortium (Tables 2 and 3A, 3B, 3C, 7A and 7B). Chemical excipients include, without limitation, (1) ferrous sulfide (125 μM)[1,4,5] and (2) L-cysteine HCl (10 mM)[6,7]; additionally, (3) Lactobacillus acidophilus ($10^{10}$ CFU), a facultative anaerobe widely used in probiotics[8,9], will be used as a biological excipient both with and without the chemical excipients. To ensure quality control, we can utilize a freeze-drying indicator (OPS Diagnostics, Lebanon, N.J.), which is a colorimetric indicator that turns from red to blue when the water content is below 2%, to confirm that the sample has been properly lyophilized. Additionally, during process development we will include a phosphorescence-based oxygen nanoprobe that will be used to determine the shelf life of the gelatin capsule and confirm anaerobic conditions within the lyophilized mixture. All preparation will be performed in an anaerobic chamber (Coy Labs, Grass Lake, Mich.) under sterile technique.

TABLE 5

List of different excipients (single and combination) for use with lyophilized bacterial consortium.

| Excipient(s) | Concentration |
|---|---|
| Ferrous Sulfide | 125 µM |
| L-Cysteine HCl | 10 mM |
| L. acidophilus | $10^{10}$ CFU |
| Ferrous Sulfide + L-Cysteine HCl | 125 µM & 10 mM |
| Ferrous Sulfide + L. acidophilus | 125 µM & $10^{10}$ CFU |
| L-Cysteine HCl + L. acidophilus | 10 mM & $10^{10}$ CFU |
| Ferrous Sulfide + L-Cysteine HCl + L. acidophilus | 125 µM, 10 mM, & $10^{10}$ CFU |

Lyophilization, Encapsulation, and Packaging.

The solution containing the lyophilization medium, resuspended pellet, and excipient(s) will be transferred to a lyophilizer that has been flushed with nitrogen gas to maintain an anaerobic headspace. Lyophilizers are commercially available and can be obtained from BenchTop Pro with Omnitronics, SP Scientific, Warminster, Pa. for example. Lyophilization will initially be perfomed using the steps set forth below and in the following references: (ATCC. Methods for freezing and freeze-dryingbacteria. 2014. Available on the world wide web at atcc.custhelp.com/app/answers/detail/a_id/140/~/methods-for-freezing-and-freeze-drying-bacteria; Diagnostics O. Bacteria Freeze Drying Protocol. 2014. Available at: on the world wide web at.opsdiagnostics.com/notes/ranpri/rpbacteriafdprotocol.htm; Diagnostics O. Bacteria Lyophilization Overview. 2014. Available at: on the world wide web at http://opsdiagnostics.com/notes/ranpri/bacteria_lyophilization_overview.htm; Savini M, et al. Nutrients 2010; 2(3):330-9; Gitaitis R D. Refinement of Lyophilization Methodology for Storage of Large Numbers of Bacterial Strains. Plant Dis. 1987; July: 615; Simon E M, et al. Maintaining Cultures for Biotechnology and Industry. Elsevier; 1996:133-159; Jörg Overmann. Principles of enrichment, isolation, cultivation, and preservation of prokaryotes. In: Rosenberg E, DeLong E F, Lory S, Stackebrandt E, Thompson F, eds. The Prokaryotes. Berlin, Heidelberg: Springer Berlin Heidelberg; 2013; Malik K A. J. Microbiol. Methods 12:117-124 (1990).

General Lyophilization Procedure:

Cells are grown to late log or early stationary phase under optimal conditions on the medium of choice, harvested by centrifugation and the culture broth removed. The pellet is then resuspended in an in equal volume of lyophilization medium. Cells are divided into aliquots and placed into sterile vials or tubes (approximately 250-500 µl representing ~$10^8$ bacteria). The tubes are then placed in the lyophilizer for a suitable time period to ensure full lyophilization of the sample. The samples are frozen down to −40° C. When using instruments that provide for control of rate of freezing, a drop of 1° C. per minute is preferred. Once the samples reach temperature, they should be visibly frozen. The sample is then subjected to vacuum pressure for drying.

Primary drying is the longest phase of the freeze drying process. The time for primary drying will also depend upon the volume of the sample. For bacteria, samples rarely need to be large and typically are 0.25 to 0.5 ml. A limited number of samples (10-20) in a shelf dryer can be completely dried in just a couple of hours. A fully loaded dryer with several hundred samples will take longer. As a standard guide, freeze dry overnight.

Samples may still contain moisture following primary drying. The amount is variable but ranges between 2 and 4%. This moisture level can be reduced by pumping heat into the sample during the secondary drying phase. This phase is relatively short, lasting 1 to 2 hours, but important for long-term viability. With the vacuum in place, the vials are stoppered using the stoppering plate/mechanism. The vacuum is then released, the vials removed and the stoppers further secured with rubber bungs/stoppers with foil crimp seals. It is best to store the vials at 4° C. in the dark.

Optionally, the freeze dried bacteria are tested for viability as compared to the original culture and can be monitored for stability/viability of the freeze dried cultures by testing at 30, 90, 180 and 365 days.

It should be noted that these steps can optimized if necessary to ensure maximum survival of the bacterial consortium. The resulting product will be then be transferred back to the anaerobic chamber for downstream processing. The lyophilized product will be weighed (to ensure $10^{10}$ CFU/capsule) and packaged in gelatin capsules (Capsugel, Morristown, N.J.) under anaerobic conditions. These capsules will then be packaged in glass ampoules (Schott, Elmsford, N.Y.) to maintain anaerobic conditions during shipment and storage.

Viability Testing.

Robustness of the product over time will be assessed using different configurations containing single and various factorial mixtures of excipients prepared via the same lyophilization, encapsulation, and packaging procedures. Products will then be stored in the laboratory on a shelf at room temperature and tested in triplicate for viability at 0, 30, 60, 180, and 360 days from the date of production. Oxygen content will be measured via phosphorescence of the oxygen nanoprobe on a bi-weekly basis (Albenberg L, Esipova T V, Judge C P, et al. Correlation Between Intraluminal Oxygen Gradient and Radial Partitioning of Intestinal Microbiota in Humans and Mice. Gastroenterology 2014). Validation will be performed by breaking the ampoule under aerobic conditions (as would be encountered when delivering the capsule to a subject in a medical setting) and then placing the gel capsule in pre-reduced culture medium (same medium as was used to grow the initial liquid cultures). Growth can be measured using optical density ($OD_{600}$) and colony counting (CFU/mL) at six hour time points up to three days after inoculation. This will ensure viability of the consortium for delivery to a human subject via this method over a continuous five day dosage period.

Alternative Method Development. Concurrently with methods for production of gel capsules containing lyophilized cultures, we will also freeze large liquid volumes containing viable cells to be thawed and administered via colonoscopy, endoscopy, enteroscopy, enema or nasoduodenal tube. In brief, liquid cultures will be centrifuged, the pellets will be resuspended in a nutrient-rich broth (ATCC. ATCC® Bacterial Culture Guide Tips and Techniques for Culturing Bacteria and Bacteriophages Table of Contents. Manassas, Va.: Available on the world wide web at atcc.org/~/media/PDFs/Culture Guides/Previews/ATCC_Bacterial_Culture_Guide_Preview.ashx.) (containing 10% glucose and 10% skim milk as cryoprotectants (Hubálek Z. Protectants used in the cryopreservation of microorganisms. Cryobiology 2003; 46(3):205-229. doi:10.1016/S0011-2240 (03)00046-4; Moore L W, Carlson R V. Liqquid Nitrogen Storage of Phytopathogenic Bacteria. Phytopathology 1987; 65:246-250), and 10 mM L-cysteine HCl as an oxygen scavenger), and stored at −80° C. in sealed syringes within secondary containment in pre-measured doses. For administration to subjects, the samples will be thawed and the syringes will be attached directly to the delivery mechanism (i.e., enema or NG tube) to minimize oxygen contamination.
Exemplary Regimen to Reduce the Concentration of Gut Bacteria Prior to Administration of Microbial Consortium in a Patient in Need Thereof Prior to initial administration of microbial consortium, it may be necessary to reduce the concentration of bacteria within the intestinal lumen. Prior research has demonstrated that a single antibiotic does not appreciably reduce total bacteria concentration within feces although some antibiotics (e.g. vancomycin) dramatically alter the composition of the gut microbiota (Vrieze J Hepatol 2014; 60:824-31). Furthermore, not all combinations of orally administered antibiotics can reduce the concentration of bacteria within the gut lumen. For example, a combination of rifaximin 550 mg orally twice daily plus metronidazole 500 mg orally twice daily plus trimethoprim-sulfamethoxazole (160 mg-800 mg) orally twice daily for three days results in minimal change in total fecal bacterial concentration (p>0.4 paired t-test, n=5 human subjects). Reduction in the concentration of bacteria within the gut lumen prior to the administration of microbial consortium is accomplished with a combination of antibiotics that are effective within the intestinal lumen, dietary modification and a bowel lavage to reduce the fecal biomass. During the first 3 days, adult patients will consume vancomycin 500 mg orally every 6 hours and neomycin 1000 mg orally every 6 hours. The dose for children must be reduced according to the child's weight (vancomycin 40 mg/kg/day in 4 divided doses, not to exceed 500 mg PO every 6 hours; neomycin 25 mg/kg/dose PO every 8 hours, not to exceed 1 gram PO every 8 hours). On the second day patients consume only a clear liquid diet followed by 2-4 L of polyethylene glycol based bowel purgative (such as GoLytely®). Slight variation in the preparation regimen is possible, particularly with respect to the timing of administration of the polyethylene glycol based bowel purge. This can be administered on either the $2^{nd}$ or the $3^{rd}$ day of the regimen. Similarly, smaller volume polyethylene glycol bowel purgatives can be combined with oral laxatives such as bisacodyl.

Following the antibiotic and PEG bowel cleansing protocol, the microbial consortium will be inoculated either orally via a capsule, into the upper GI track via a nasoduodenal tube, endoscopy or enteroscopy or into the lower GI tract via a colonoscopy or enema. The inoculation will be a minimum of one day but may be repeated daily for a maximum of 7 days.

The preparation regimen is not required for chronic dosing of microbial consortium. However, following a lapse in therapy the bowel preparation regimen may be required prior to re-initiation of therapy.

Kits

The invention provides kits for promoting the expansion of a defined microbial consortia in the gut of a host. In particular embodiments, the kit comprises a sterile container which contains a therapeutic or prophylactic composition comprising the defined microbial consortia; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments. The kit may also contain the gelatin capsules described above and instructions for methods of administration.

The kit preferably contains instructions that generally include information about the use of the composition for the expansion of the microbial consortia in the gut of the subject. The kit further contains precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the microbial consortia, formulation methods, screening assays, and therapeutic methods of the invention, and are not intended to limit the scope of what the inventors regard as their invention.

EXAMPLES

Example 1

Figure 1B:
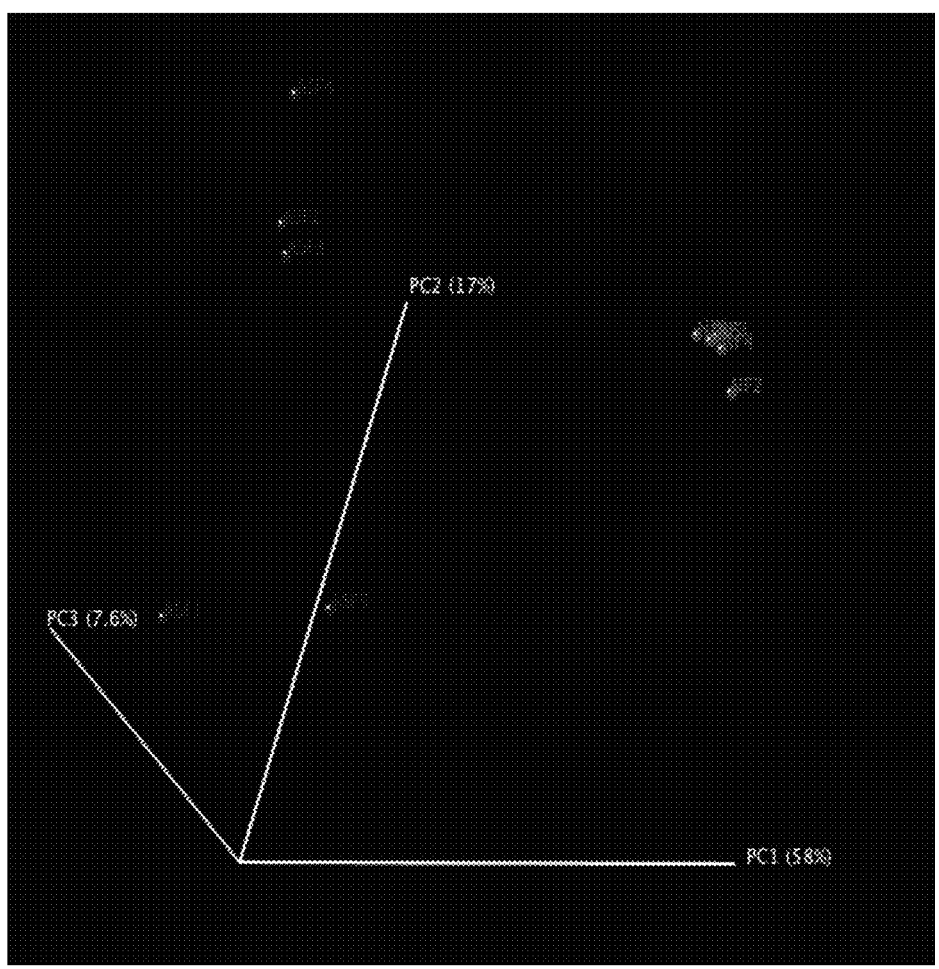
Figure 1C:
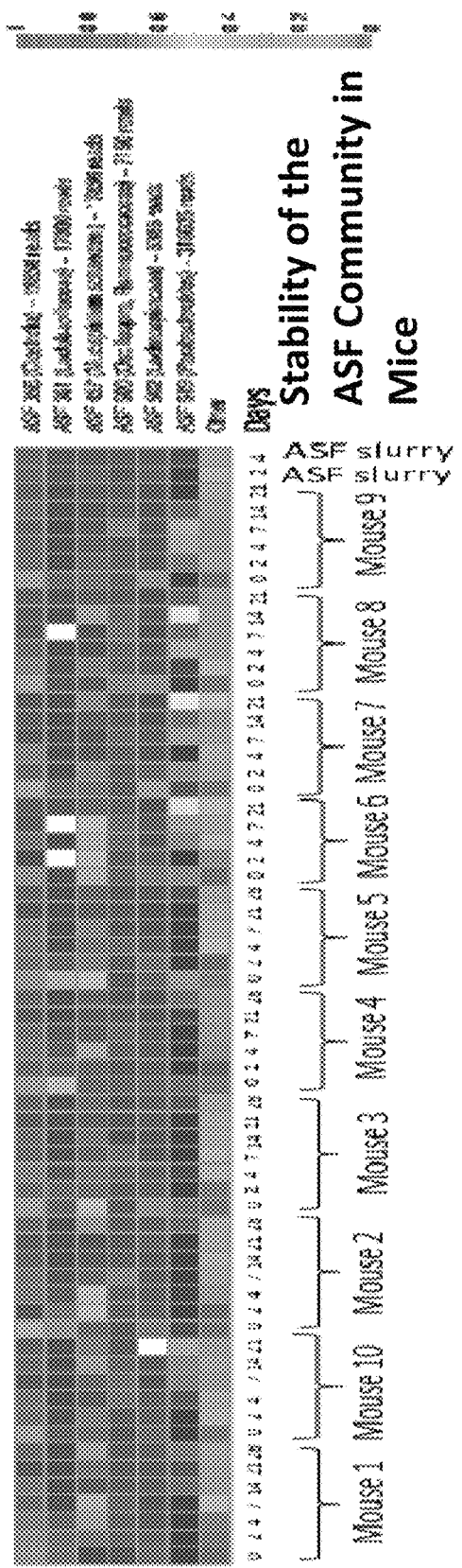

ASF is a Distinctive Gut Microbial Community that Exhibited Resiliency Under SPF Housing Conditions ASF consists of 8 bacterial strains developed in the 1970s that are collectively known to induce immune tolerance, and are currently used commercially to colonize immune deficient mice to maintain health. To characterize potential donors containing the ASF community, 16S rRNA gene sequencing was performed on fecal DNA obtained from ASF colonized mice housed in an isolator. Although there was only a small reduction in the overall abundance of bacteria in the ASF community relative to mice with conventional microbiota (FIG. 1A), the ASF community could be visualized as a very distinctive community on a UniFrac-based PCoA analysis (FIG. 1B). To determine the resiliency of the ASF in mice housed in SPF conditions, sequential fecal pellets were collected from ten mice for analysis by 16S rRNA sequencing (FIG. 1C). Six taxa were resolved at the depth of sequencing performed with *Parabacteroides* being the dominant component of ASF accounting for roughly 90% of sequence reads at the time of transfer of mice from an isolator to SPF conditions. At 28 days, *Parabacteroides* remained the dominant taxon with the other 5 ASF members being present along with the appearance of "other" non-ASF taxa accounting for approximately 20-30% of reads indicating a moderate level of ASF resiliency to disruption by other gut bacteria.

Example 2

Figure 2A:
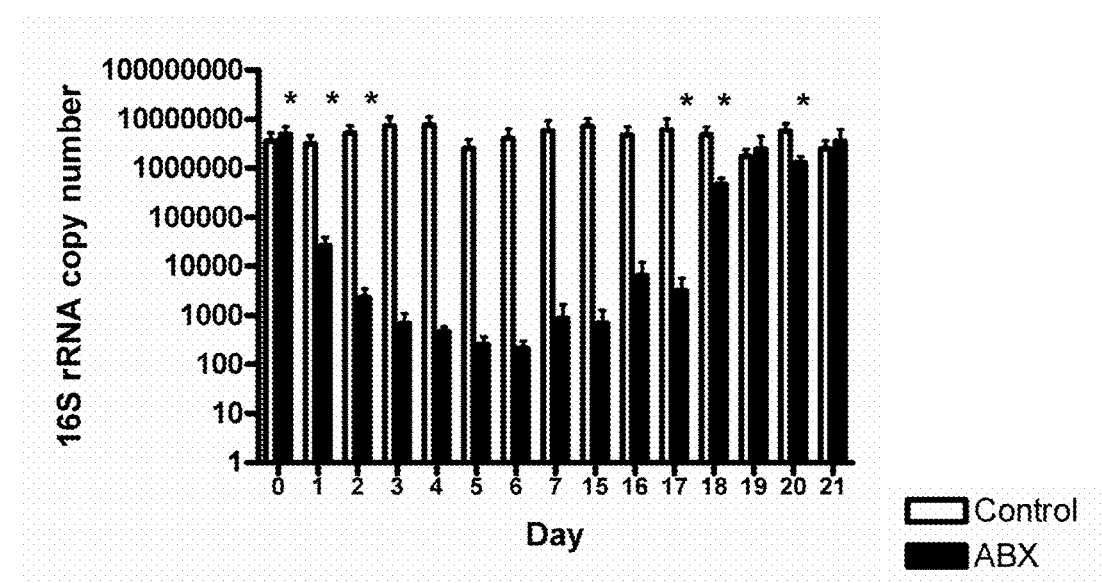
FIGS. 2A-2C show the development of a method for FMT in mice.
Figure 2B:
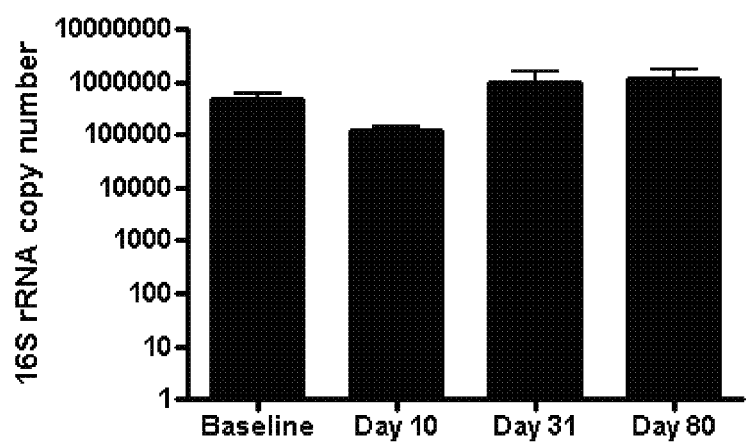
Figure 2C:
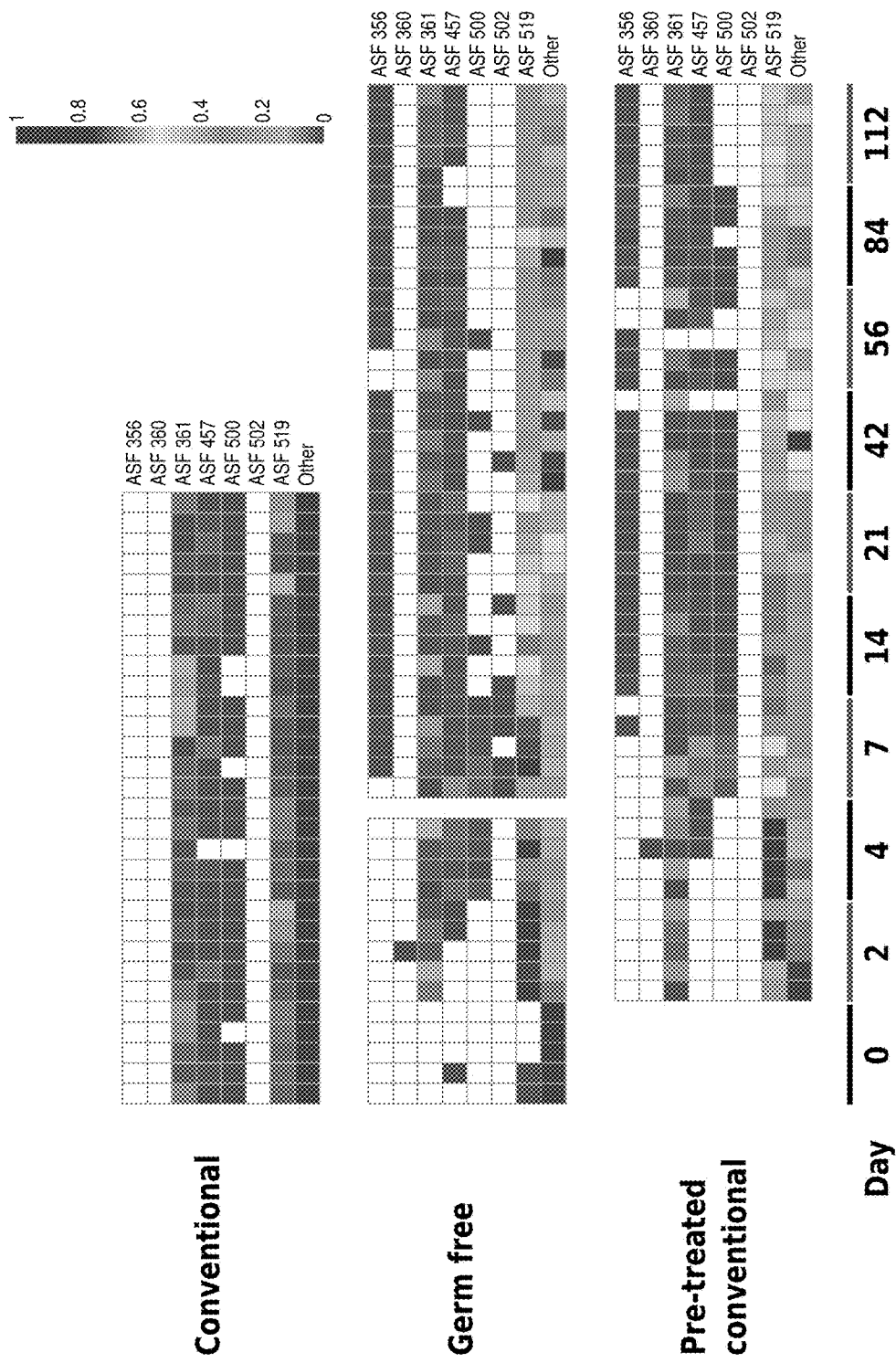

Preparation of Mice with Antibiotics and Polyethylene Glycol Allows the Transplantation of ASF into Previously Colonized Mice Mixed results have been reported regarding the transfer of conventional microbiota between rodents with some sources reporting successful transfer with repetitive inoculation, while others report that the use of antibiotics prevents effective transfer. Reasoning that significant reduction of the endogenous conventional microbiota would be needed for effective transfer of ASF due to its reduced membership, studies were performed to determine the optimal timing of microbiota transfer based on the response of conventional microbiota to the oral delivery of two non-absorbable antibiotics, neomycin and vancomycin. A maximal reduction of 16S rRNA copy number by approximately 4 logs was achieved within 72 hours of oral antibiotic initiation with the return of 16S rRNA copy number to baseline 5 days after discontinuing antibiotics (FIG. 2A). Having defined a time window for the optimal introduction of ASF, fecal slurries of ASF obtained from ASF colonized mice (Taconic) were sequentially gavaged into conventionally housed recipients for seven days following a 72 hour treatment with oral antibiotics and a 24 hour intestinal purge using polyethene glycol (pretreated conventional). The results demonstrating the effectiveness of ASF transfer into these recipients and its resilience over the next 21 days, relative to conventionally housed mice without pretreatment and germ-free recipients, are shown in FIG. 2B and FIG. 2C, where 16S copy number after transplantation has been restored to baseline levels after ASR transplantation (FIG. 2B). While no transfer of ASF was observed in conventionally housed mice that did not receive the pretreatment, ASF transfer was as effective in pretreated conventionally housed as germ-free recipients (FIG. 2C). Interestingly, the ASF consortium was more resilient over 21 days in the pretreated conventional mice than in the germ-free recipients.

Example 3

Figure 3A:
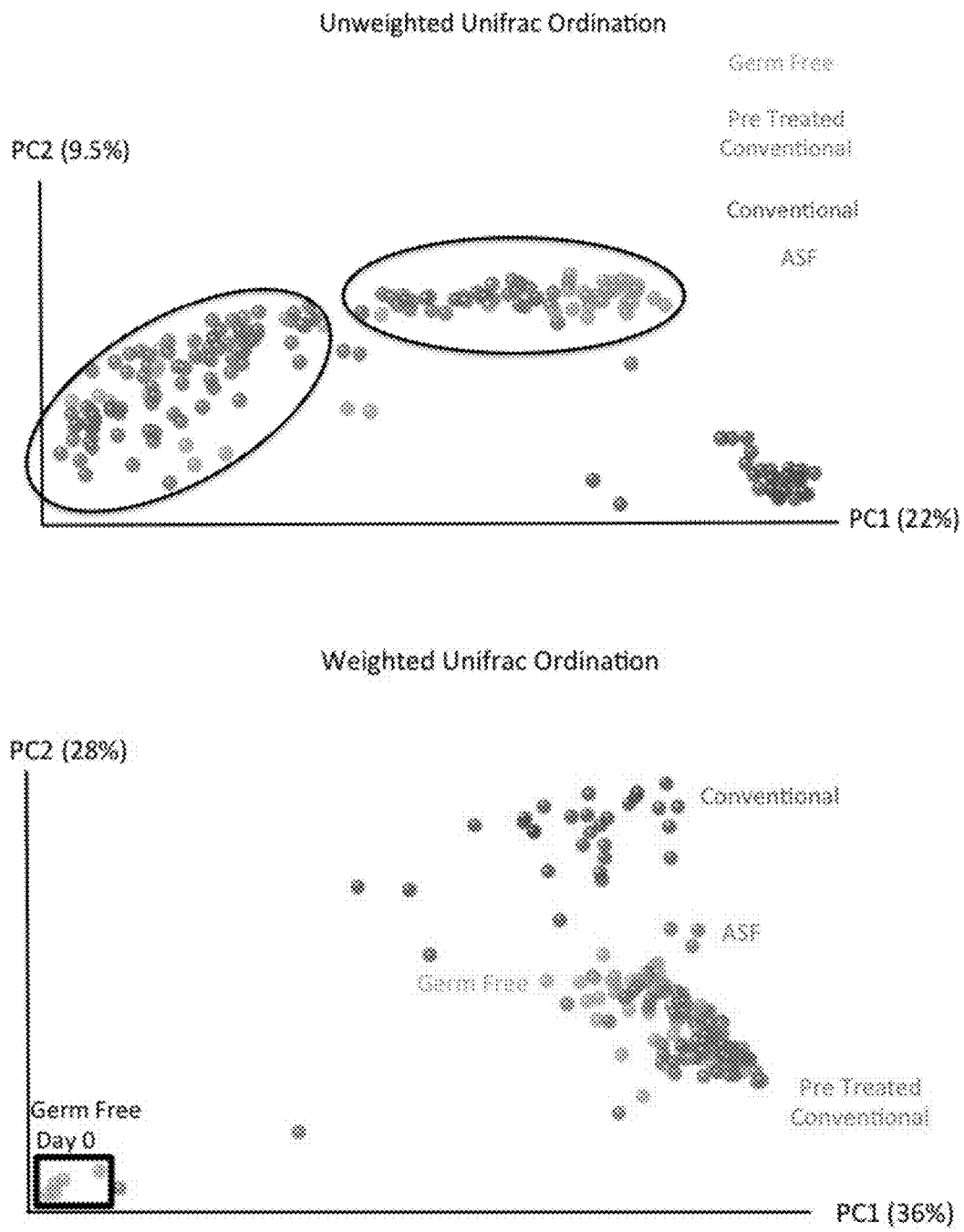
FIG. 3A provides diagrams showing long-term taxonomic resiliency of the transplanted ASF community over four months evaluated by both unweighted Unifrac (presence-absence of taxa) and weighted Unifrac.
Figure 3B:
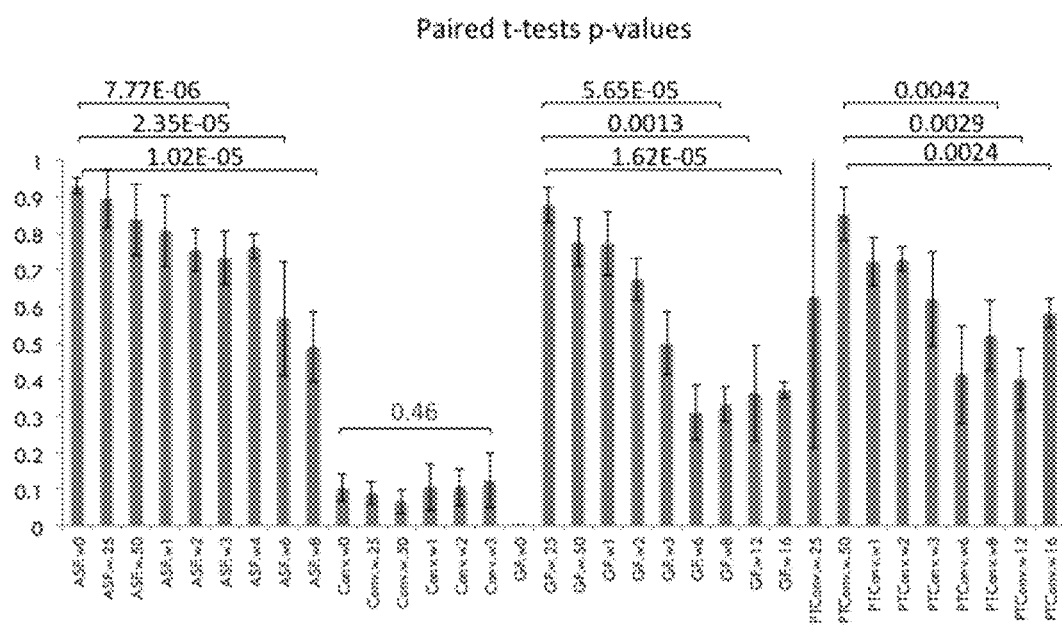
FIG. 3B shows that ASF sequence reads remained stable at six weeks relative to ASF levels observed in conventionally-housed mice. Essentially, a new steady state develops with ASF and *Clostridial taxa* (FIG. 4B) that exhibits long-lasting reduction of urease activity and ammonia production (FIG. 6).
Figure 4A:
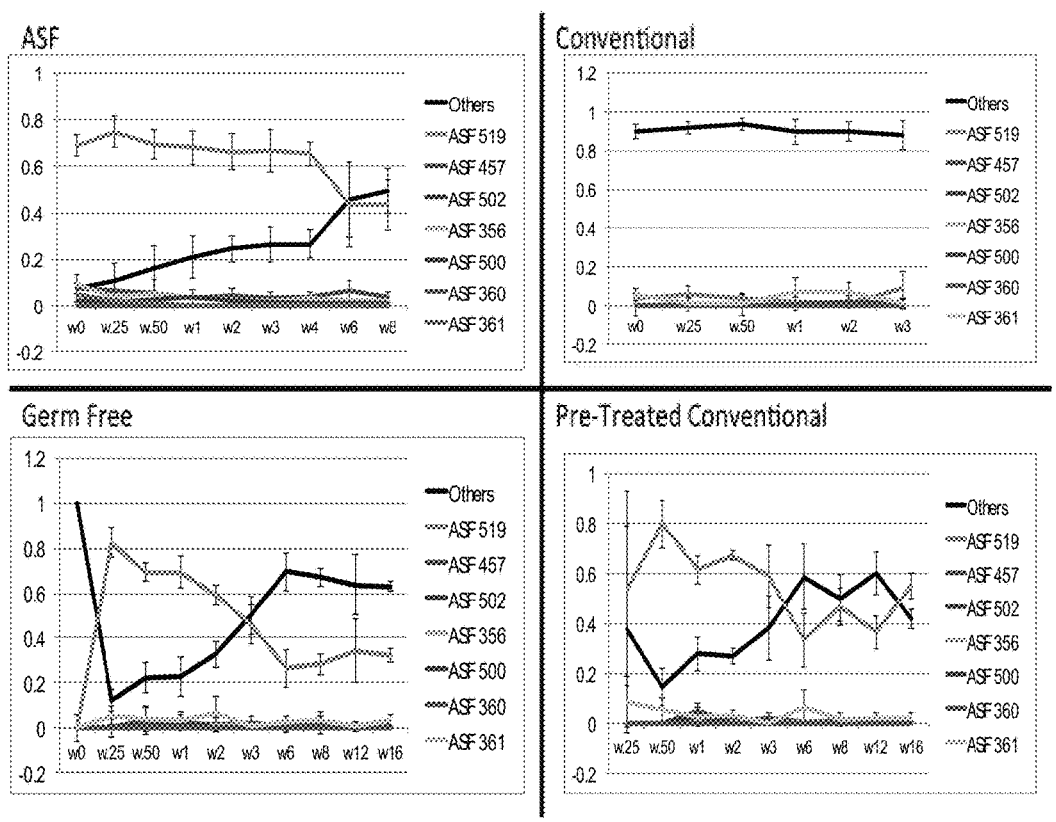
FIG. 4A provides four graphs showing that the resilience of the ASF community was determined by the persistence of Paracteroides in both germ-free and pretreated conventional hosts where this taxon remained stable after about one month.

Long-Term Taxonomic Resilience of the Transplanted ASF Community Established by the Ability of *Parabacteroides* to Inhibit Invasion of *Bacteroides*, but not *Clostridia* Genera into the Gut Microbiota Niche Long-term taxonomic resiliency of the transplanted ASF community over four months evaluated by both unweighted Unifrac (presence-absence of taxa, FIG. 3A) and weighted Unifrac (relative abundance, FIG. 3A), revealed that the transplanted community rapidly established a new intermediate steady state in between the ASF inoculum and the conventional, pre-treatment community. The proportion of ASF sequence reads remained relatively stable after six weeks at approximately 40% in germ-free recipients and 50% in pretreatment conventional hosts both considerably greater than the 10% proportion of ASF community members normally observed in conventionally-housed mice (FIG. 3B). Resilience of the ASF community was largely determined by the persistence of Paracteroides in both germ-free and pretreated conventional hosts where this taxon remained stable after about one month (FIG. 4A). The temporal relationship between *Parabacteroides* and "others" was remarkably similar in both ASF colonized mice and pretreated conventional hosts showing that the new steady state of the ASF community in transplanted mice was due to the SPF environment in which the host resides and is not a manifestation of the transplantation procedure.

Figure 4B:
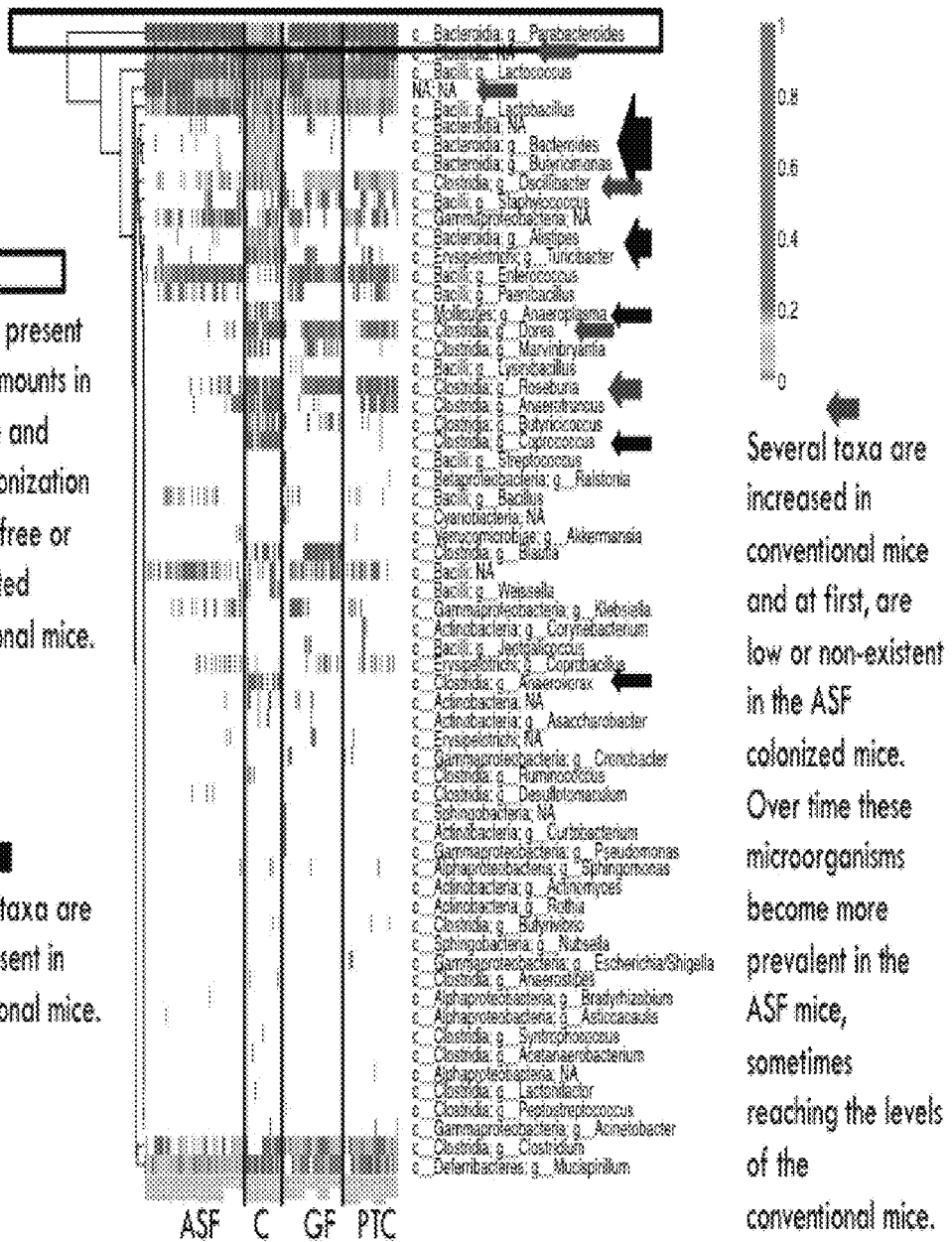
FIG. 4B shows that resilience of the ASF community was determined by the persistence of Paracteroides in germ-free and pretreated conventional hosts. It also demonstrates that specific bacterial taxa, predominantly *Clostridia*, appear over time to develop a stable new steady state with ASF that lacks urease activity and ammonia production.

As is common in humans, the bacteria in the *Bacteroides* genus are the dominant taxa in conventionally housed mice. Upon transplantation of ASF into either germ-free or pretreated conventional hosts the ASF community persists, but specific organisms from the pretransplant community slowly increase in abundance (FIG. 4B). Rather than being stochastic, the bacterial taxa capable of time-dependent displacement of the ASF community were specific taxa primarily from the *Clostridium* genus. Thus, *Parabacteroides* maintained its niche in the gut as the predominant representative of the *Bacteroidetes* phylum, but an equilibrium was established with the *Firmicutes phylum* primarily composed of the *Clostridium* genus.

Example 4

ASF has Minimal Urease Gene Representation and Enzymatic Activity

Figure 5A:
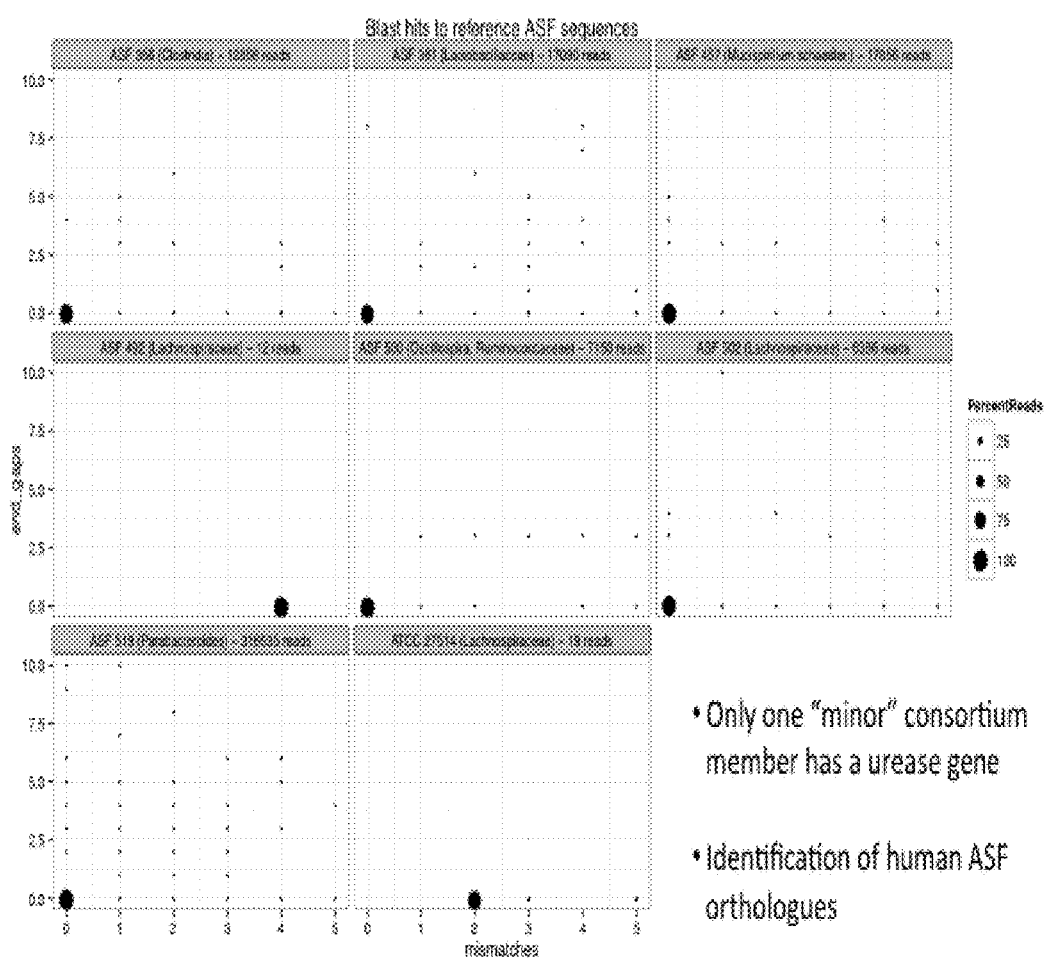

The lack of a mammalian urease gene makes the hydrolysis of urea a microbiota-specific function whereby the subsequent production of ammonia is shared between the host and gut microbiota for utilization in protein synthesis. Ammonia is also largely responsible for the alkaline pH of the colonic luminal environment acting to buffer the short chain fatty acids produced by the microbiota fermentation of diet and host derived glycans. Genomic sequencing of the ASF community revealed minimal gene representation in the total community with no urease gene identified in the *Parabacteroides* genome (FIG. 5A). To establish the lack of urease enzymatic activity as a functional characteristic of the ASF community that potentially impacts the gut microbiota and host metabolome, both ex vivo and in vivo urease activity assays were performed. Fecal urease activity (FIG. 5B) was undetectable and ammonia levels were minimal (FIG. 5C) in fecal pellets collected from mice colonized with ASF. Using intravenously delivered $^{13}$C-urea to quantify urease activity in vivo through the production of $^{13}CO_2$ in a breath test, this directly demonstrated that urea delivered by the host undergoes minimal hydrolysis in ASF colonized mice (FIG. 5D). Consistent with the long-term displacement of *Bacteroides* by *Parabacteroides* after transplantation, fecal urease activity remained dramatically reduced for at least four months in pretreated conventional transplanted mice demonstrating both the taxonomic and functional resilience of the ASF community (FIG. 6).

Example 5

Figure 7:
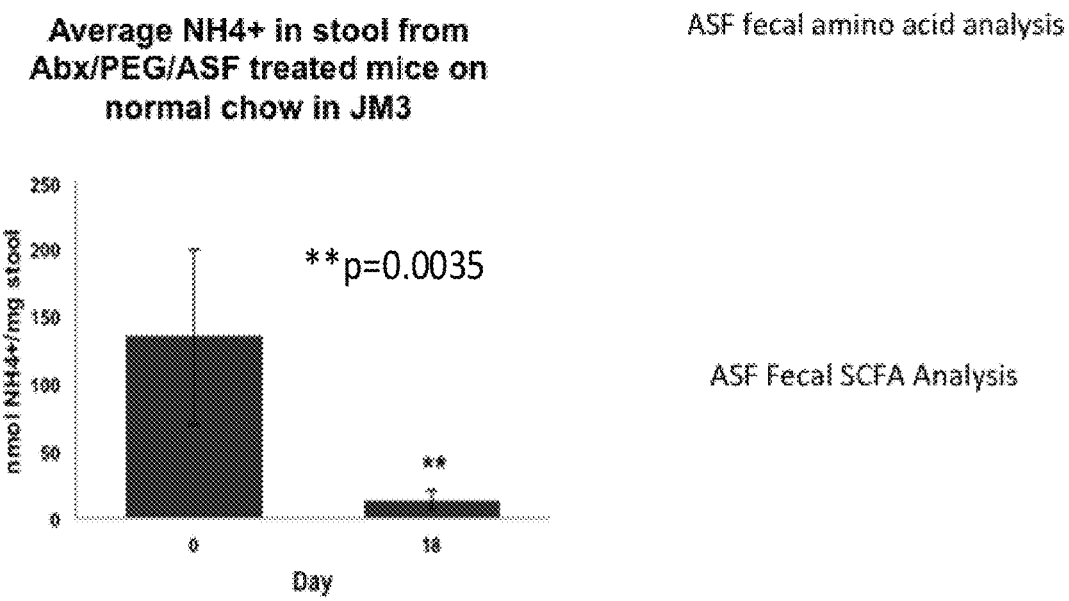
FIG. 7 shows ammonia levels in the stool of mice treated with antibiotics, polyethylene glycol (PEG), and ASF.
Figure 8:
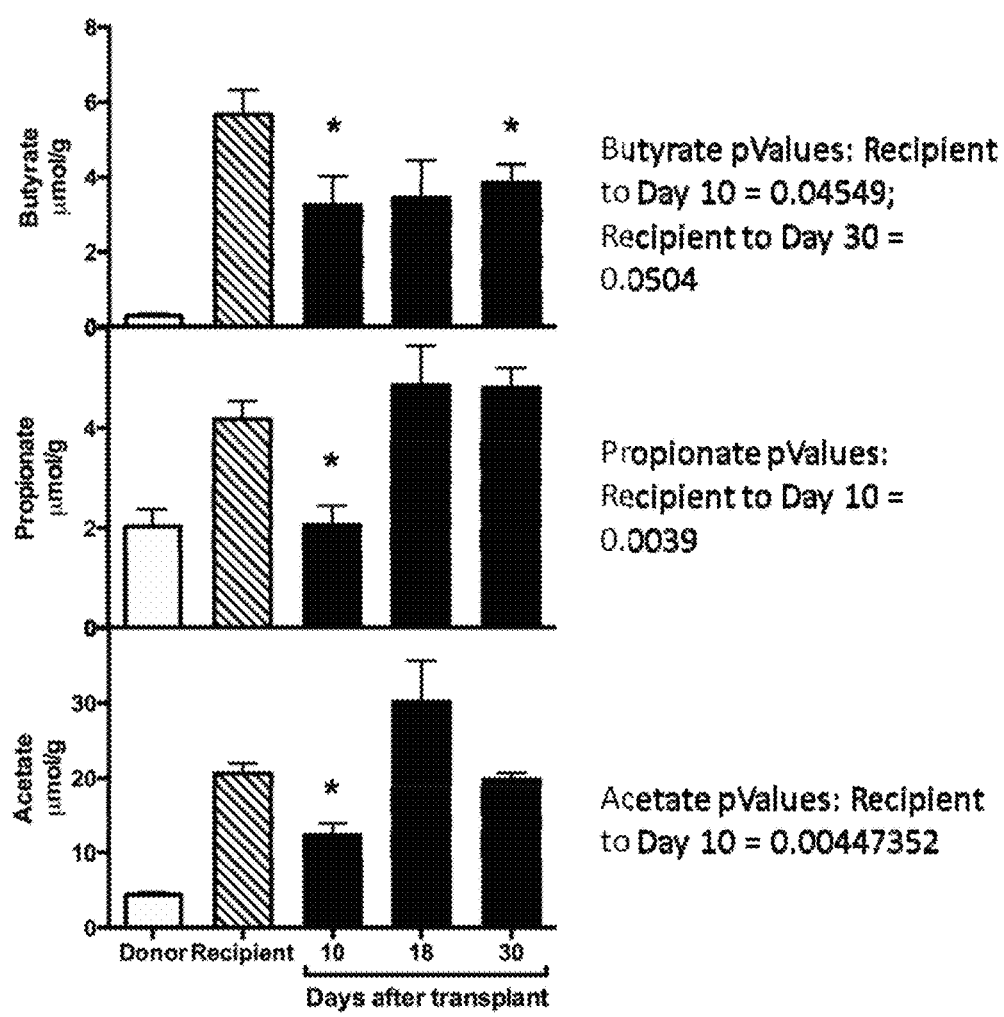
FIG. 8 shows, through the course of time, the levels of butyrate, propionate and acetate in the stool of mice treated with antibiotics, polyethylene glycol (PEG), and ASF.

The ASF Community and Transplanted Mice are Both Deficient in Essential Amino Acids The question of whether the decreased urease activity and ammonia production of the ASF community would reduce the production of amino acids by the gut microbiota and their availability to the host was explored. The latter is particularly relevant in rodents where corprophagia has been shown to be important to maintain essential amino acid levels. Transplantation of ASF into pretreated conventional mice led to a significant reduction in fecal ammonia levels (FIG. 7). A metabolomic analysis of fecal pellets prior to and after ASF transplantation revealed that ASF transplantation is not able to alter butyrate production in a durable fashion in contrast to ammonia (FIG. 8). This result highlights the exclusive ability of the invention herein to reprogram the metabolome of the gut microbiota by specifically the targeting nitrogen balance.

To further evaluate the effect of ASF transplantation on host nitrogen balance, plasma amino acid profiling was performed on both the portal and arterial circulation with the notion that the portal-systemic ratio of amino acid levels would be indicative of compensatory hepatic responses needed to maintain nitrogen homeostasis.

In the portal circulation, the levels of nearly all essential amino acids were significantly reduced after ASF transplantation, the only exception being tryptophan which remained unchanged. This profile was nearly identical to that in the arterial circulation indicating a systemic deficiency of essential amino acid levels after ASF transplantation for which the liver was unable to compensate. By contrast, ASF transplantation led to a significant reduction of three nonessential amino acids in the portal circulation with only one, threonine, remaining significantly reduced in the arterial circulation. These results demonstrate that urease activity is critical to maintain host essential amino acid levels (Table 6).

An alternative explanation for the beneficial effects of ASF transplantation in the treatment of hepatic encephalopathy would be the effects of this newly developed gut microbiota steady state on plasma amino acid levels. Several essential amino acids, those that cannot be synthesized de novo by the host and must be obtained through diet, have been hypothesized to play an important role in the pathogenesis of HE. Among the essential amino acids are the aromatic amino acids including phenylalanine, tyrosine (which is only conditionally essential as it is formed from phenylalanine), and tryptophan. These aromatic amino acids are precursors to biogenic amines that are neurotransmitters such as catecholamines and serotonin as well as false neurotransmitters including phenylethanolamine, octopamine, and synephrine. Normally aromatic amino acids are decarboxylated to their respective amines, which subsequently undergo additional metabolism in the liver by monoamine oxidase into aldehydes and ammonia. When hepatic function is impaired as in acute liver failure, the precursor aromatic amino acids and their amines are shunted away from the pathway of aldehyde formation and may enter the central nervous system to become locally B-hydroxylated into false neurotransmitters and replace normal neurotransmitters[20]. During hepatic failure, it is well known that plasma levels of aromatic amino acids (AAA) are increased whereas branch chain amino acids (BCAA) are decreased. Fischer et al. proposed that the ratio of BCAA to AAA (BCAA/AAA=(valine)+(leucine)+(isoleucine)/(phenylalanine)+(tyrosine)) would be predictive of HE[21]. Indeed, numerous reports have verified that a decrease in this ratio is associated with hepatic dysfunction[22]. ASF colonization led to a remarkable alteration in plasma levels of essential amino acids with a significantly higher Fischer's Ratio (3.87) relative to mice with a conventional microbiota (2.68, $p<0.01$). In total, these results support the additional notion that ASF colonization may also protect against morbidity and mortality associated with liver failure by altering plasma essential amino acids and the subsequent production of false neurotransmitters.

TABLE 6

Table 6. Concentrations (nmol/mL) of essential amino acids from sera in control and ASF FMT mice (n = 5 in each group, *$p < 0.05$ compared to control, **$p < 0.01$ compared to control).

|  | Portal Blood | | Arterial Blood | |
| --- | --- | --- | --- | --- |
|  | Control Mean (±SD) | ASF Mean (±SD) | Control Mean (±SD) | ASF Mean (±SD) |
| THR | 173.01 (±33.87) | 72.88 (±31.52)** | 169.43 (±27.44) | 84.49 (±5.49)** |
| TRYP | 81.44 (±5.81) | 80.17 (±33.48) | 58.13 (±6.88) | 59.28 (±14.22) |
| METH | 58.35 (±10.55) | 28.84 (±12.12)** | 57.32 (±17.42) | 30.63 (±3.45)** |
| VAL | 217.04 (±51.15) | 136.52 (±60.12)* | 189.31 (±45.25) | 135.56 (±14.46)* |
| PHE | 57.88 (±10.55) | 41.00 (±17.75)* | 56.96 (±17.67) | 44.30 (±2.89) |
| ILE | 143.39 (±35.79) | 62.36 (±27.54)** | 118.76 (±32.63) | 59.64 (±6.97)** |
| LEU | 186.46 (±50.75) | 110.01 (±49.52)* | 159.55 (±47.15) | 108.21 (±13.48)* |
| ORN | 83.05 (±17.03) | 47.01 (±25.14)* | 162.16 (±14.37) | 89.12 (±7.29)** |
| LYS | 201.82 (±29.65) | 105.16 (±48.92)** | 206.66 (±50.26) | 120.57 (±21.52)** |
| TYR | 140.02 (±29.99) | 36.10 (±15.51)** | 116.46 (±21.19) | 34.30 (±4.84)** |

Example 6

Figure 9A:
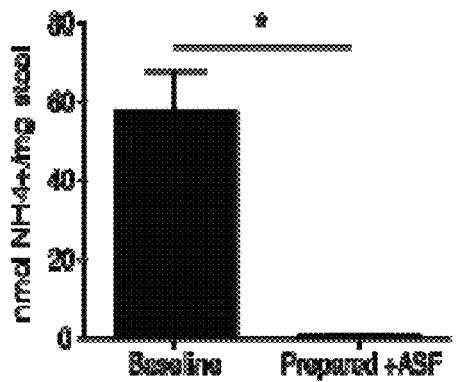
FIGS. 9A-9D show fecal ammonia levels, mortality rates and histology associated with TAA induced hepatic injury studies.

ASF Transplantation Reduced Cognitive Impairment and Mortality in a Murine Model of Acute Liver Injury A major cause of morbidity and mortality associated with acute liver injury is the development of hepatic encephalopathy (HE). Since hyperammonemia is associated with the development of HE in patients with impaired hepatic function (8), we asked if the transplantation of ASF might mitigate the effects of acute hepatic injury induced by thioacetamide (TAA)(23) treatment. Prepared ASF-transplanted mice showed both a reduction in fecal ammonia levels (FIG. 9A) and reduced mortality in response to high dose TAA compared to mice with conventional microbiota (FIG. 10A).

Figure 9B:
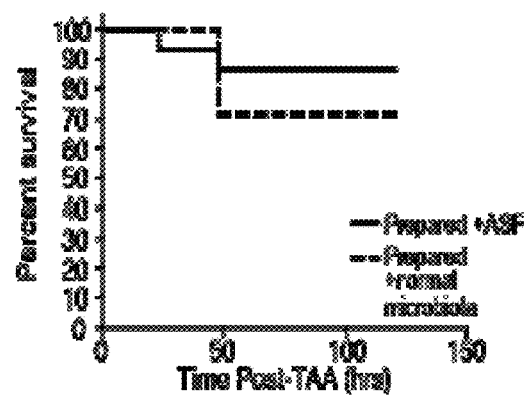
Figure 9C:
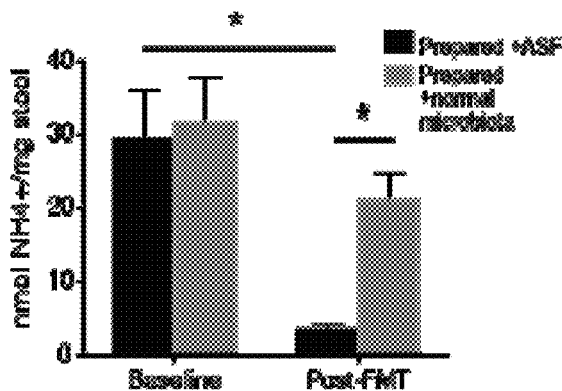
Figure 9D:
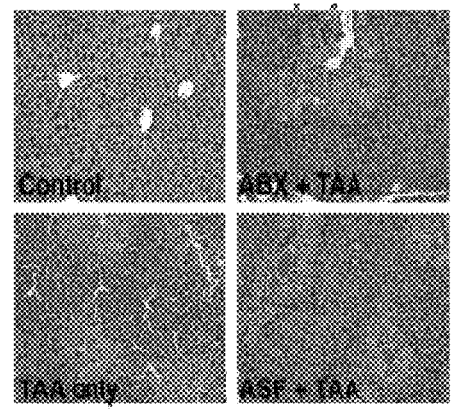
Figure 11A:
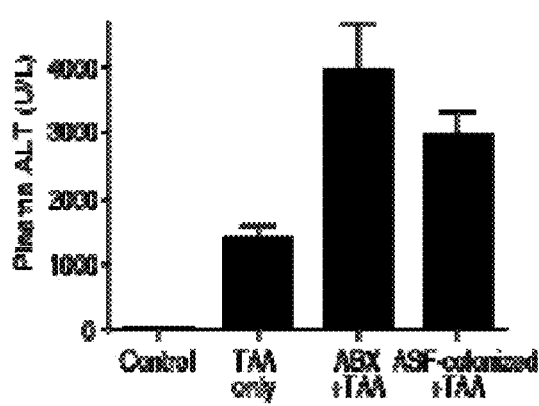
FIGS. 11A and 11B show differential liver injury does not explain differences with or without ASF.
Figure 11B:
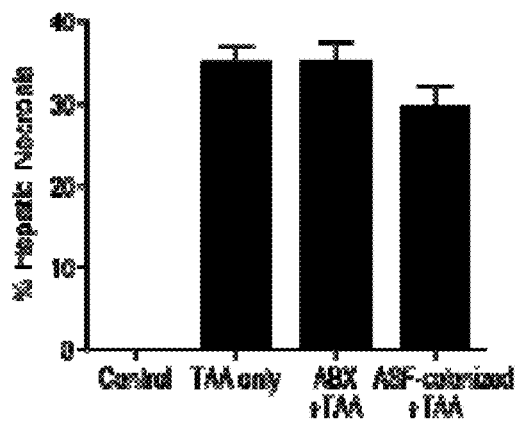
Figure 12:
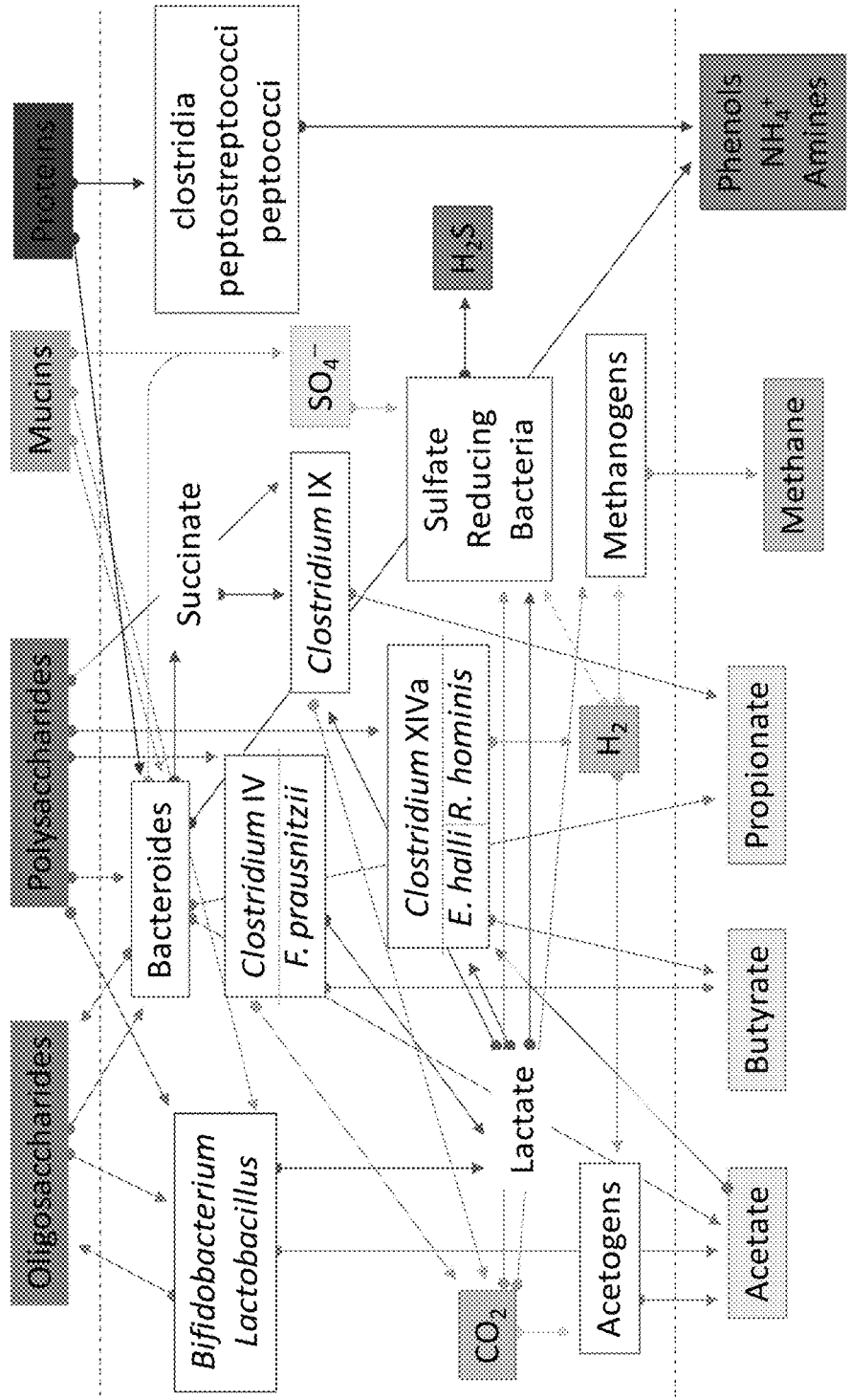
FIG. 12 shows a schematic diagram of the gut microbiota.

In mice, the TAA model has also been associated neurobehavioral abnormalities resembling hepatic encephalopathy in humans (24). Using a lower dose of TAA to reduce mortality, we analyzed memory and spatial learning in a Y-maze test comparing ASF transplanted mice to mice transplanted with normal feces (NF) as a control (25). The survival rates were similar between the two groups at 80-90% at the lower TAA dose (FIG. 9B). Fecal ammonia levels were reduced in mice transplanted with ASF compared to NF (FIG. 9C). TAA treated mice transplanted with NF showed a decrease in cognitive function, quantified as spontaneous alternations in a Y-maze test, whereas ASF treated mice were not different from untreated controls (FIG. 10B). A possible alternative could be that ASF transplantation directly reduced liver injury. We tested this by monitoring plasma alanine aminotransferase (ALT) and quantifying histologic evidence of hepatocyte necrosis (FIG. 11A and FIG. 11B). Both revealed that liver damage induced by TAA was not reduced by either ASF transplantation or ABX treatment. Thus improved survival and behavioral performance were associated with reduced ammonia levels and not reduced liver injury.

The success of FMT in the treatment of *Clostridial difficile* infection supports the concept of a resilient microbial community that, when transferred into a host with disease, can be therapeutic by altering a dysbiotic microbiota. However, since feces contains not only bacteria but also a multitude of archaeal, fungi, and viruses that have been poorly characterized and can change in ways that cannot be predicted, there is significant concern for both short- and long-term risks of FMT in humans. Although it is reasonable to perform FMT for refractory *Clostridial difficile* infections, there are obvious advantages to ultimately developing defined microbial consortia with defined biological properties that respond to the gut environment in predictable ways to prevent the transfer of infectious pathogens and reduce long-term risks. Using ASF as a well-characterized, innocuous microbial community with beneficial immunologic properties provided evidence of efficient transfer into previously a colonized host and model both its taxonomic and functional resiliency over time with the host in a SPF environment. Importantly, the highly distinctive clustering of the eight ASF organisms as a consortium relative to the conventional mouse microbiota, allowed us to track the effectiveness of ASF transfer as well as resiliency over time with a level of precision.

The composition of ASF has been recently described with greater precision based on 16S rRNA gene phylotyping. The ASF community remains relatively stable with *Parabacteroides* remaining the dominant taxon over one month in SPF house mice.

Although transfer of an entire gut microbiota can be achieved through repetitive inoculation of a previously colonized host without pre-treatment, and another study reports the deleterious effect of antibiotics in the transfer of the gut microbiota, reduction of the endogenous gut microbiota is preferably reduced by oral antibiotic treatment with polyethylene glycol (PEG) for efficient transfer of a defined community of only eight organisms. The transfer of ASF into conventionally housed mice (pre-treated conventional) was as effective as into germ-free recipients. This mirrors the results of FMT in humans where the use of antibiotics and PEG is used, especially where human feces has been delivered into the upper gastro-intestinal (GI) tract via a nasoduodenal tube. The succession of ASF engraftment can be evaluated by the examination of the early time points during and after the inoculation of ASF. The lactobacilli genus is present in most mice prior to transfer but a number of the low abundance ASF taxa, Mucispirilum, Oscilospria, and Lachnospariceae, appear with repetitive gavage in both germ free and pre-treated conventional hosts. The last to appear is the *Clostridial* genus at day 14 in the latter hosts, one week after gavaging was complete perhaps indicating the need for the establishment of a specific niche that permits the establishment of more fastidious taxa.

By monitoring the composition of the transplanted ASF community over four months by 16S rRNA gene sequencing, its longitudinal resiliency to the environmental stress of the host being hosted in a SPF environment was assessed. In microbial ecology terms, resilience can be defined as the amount of stress or pertubation that a system can tolerate before its trajectory changes towards a different equilibrium. The use of antibiotics in the pre-treated conventional hosts is an extreme example of an environmental stress that not only disrupts the relative abundance of taxa in the gut microbiota as previously described, but also dramatically reduces the total abundance of bacteria by at least four logs thus permitting the engraftment of the ASF community. Housing of the host in an SPF environment is much less extreme but, nevertheless, has an impact on the resilience of the implanted ASF community. Although able to engraft into both germ-free and pre-treated conventional hosts, short-term resiliency of the pure ASF community is limited as "other" taxa begin to appear within four weeks of inoculation even as some low abundance ASF members, like *Clostridia*, begin to appear. This leads to rapid establishment of a new steady state, whereby both types of transplanted hosts resemble the gut microbiota of ASF colonized mice housed long-term in an SPF environment largely driven by the ability of *Parabacteroides* to remain a dominant taxon. Possibly due to the well-described inflammatory response associated with the maturation of the mucosal immune system upon colonization, ASF is least resilient long-term when inoculated into a germ-free host.

Species rich communities tend to exhibit enhanced resiliency that are less prone to invasion by new species possibly because limiting resources are used more efficiently with different species specialized to each potentially limiting resource (Yatsunenko T et al., 2012, Nature, 486.7402: 222-227). In part, this may be due to the functional redundancy of a rich microbial community whereby multiple rare species are capable to filling a niche when an abundant species is compromised by an environmental disturbance (Yatsunenko T et al., 2012, Nature, 486.7402: 222-227). The remarkable genomic similarity of the gut microbiome amongst different individuals despite significant taxonomic inter-subject variability supports this notion (Ridaura V K et al., 2013, Science 6; 341:6150). A close examination of the bacterial taxa are excluded by ASF compared to those capable of invading the gut niche over time provide two observations supportive of these concepts. First, bacterial taxa of the *Bacteroides* genus, dominant taxa in the human gut microbiota (Koren 0 et al., 2013, PLoS Comput Biol. 9(1):e1002863) and conventionally-housed mice, were largely excluded from the gut microbiota in ASF colonized mice suggesting a remarkable ability of *Parabacteroides* to exclude *Bacteroides* within the gut niche. The high level of taxonomic and functional similarity between these two genera is reminiscent of the "trade-off" between *Bacteroides* and *Prevotella* in humans that co-exclude each other within the gut niche (Faust K et al., 2012, PLoS Comput Biol 8(7): e1002606) and form the basis of previously described "enterotypes" (Koren O et al., 2013, PLoS Comput Biol. 9(1):e1002863, and Wu G D, et al., 2011, Science 334 (6052):105-8). The biological basis by which *Bacteroides* and *Parabacteroides* may co-exclude each other is unknown but may be due to competition for limiting resources and/or the production of bacteroicins.

Second, rather than being stochastic, the bacterial taxa that invade the gut niche of ASF colonized mice are time dependent, consistent between all three models, and almost exclusively involve the *Clostridium* genus collectively reducing the proportional abundance of *Parabacteroides* by about 50%. The relative proportion of *Parabacteroides* and *Clostridial* genera, representatives of the *Bacteroidetes* and *Firmicutes* phyla, establish a new steady state after about one month approximating the composition of the conventional microbiota in both humans and mice where about 90% of the bacteria taxa reside within these two phyla. Rather than being considered a disruption of the ASF community, the rise in *Clostridia* may be due to a syntrophic synergism between these two genera that increases the richness of the gut microbiota and helps to both stabilize and enhance resiliency of the ASF community long-term as observed over the course of a four months study. The impact of the transplanted ASF community on host metabolism was also evaluated. The gut microbiota and its host co-existed in a state of mutualism that, in part, involves interactions involving nutrition and metabolism. The gut microbiota, whose collective genome exceeded its mammalian host by about 150-fold, exhibited functionalities that serve as an example of collective "superorganism". One example would be the robust representation of glycan degrading genes in the microbiome responsible for the fermentation of complex carbohydrates with the production of short chain fatty acids, compounds that have important functions in host immunity and metabolism. Similarly, these results demonstrated a syntrophic co-metabolic interaction between a mammalian host and its microbiota to maintain nitrogen balance dependent upon the microbial urease gene, a functionality not present in the mammalian genome. A waste product of the mammalian host, urea is delivered to the colon where the gut microbiota scavenges nitrogen by hydrolyzing urea into carbon dioxide and ammonia, the latter of which is utilized by the gut microbiota for protein synthesis, reabsorbed by the host, or excreted in the feces.

Although the recirculation of ammonia via the portal circulation might be one mechanism by which the host may be able to preserve nitrogen stores, these data suggested that an alternative pathway may be more important. Indeed, in the absence of portally delivered ammonia from the gut microbiota, a disproportional reduction in portal glutamine levels would have been anticipated. The significant decrease of nearly all essential amino acids in both the portal and arterial circulation of mice transplanted with ASF is consistent with the consumption of a diet deficient in essential amino acids rather than a reduction in the delivery of ammonia through the portal circulation for protein synthesis in the liver. In addition to urease genes, the genome of the microbiota also permitted the synthesis of essential amino acids using ammonia as an essential substrate. Subsequent corprophagia is a well-established method by which rodents are able to obtain essential nutrients such as essential amino acids where $^{15}N$ isotope studies suggested that one quarter of leucine consumption occurs through corprophagia in rabbits.

Despite the limited role that the delivery of ammonia via the portal circulation may play in maintaining host nitrogen balance, it is of considerable consequence to patients with chronic liver disease and/or in born errors of metabolism who are predisposed to the development of hyperammonemia. In diseases such as cirrhosis or ornithine transcarbamylase deficiency, the inability of the liver to utilize ammonia delivered by the portal circulation for amino acid and/or urea synthesis results in elevated systemic circulation of ammonia with development of neurotoxicity manifested clinically as hepatic encephalopathy. The use of antibiotics to reduce the production of ammonia by the gut microbiota is one of the modalities utilized for the treatment of this disorder. Given both the taxonomic and functional resilience of the transplanted ASF community with minimal production of ammonia one year after inoculation into previously colonized hosts, we propose that a humanized version of ASF will have utility in the treatment of these disorders.

Example 7

A Single Bacterial Species Lacking a Urease Gene can Significantly Reduce Fecal Ammonia Levels when Inoculated into a Properly Prepared Host Engineering the gut microbiota for therapeutic modulation of host metabolism is an emerging goal of microbiome research. In the previous examples, we describe methods by which we can engineer the gut microbiota in mice for therapeutic reduction of urease activity. Depletion of the pre-existing gut microbiota followed by inoculation with Altered Schaedler's Flora (ASF), a defined consortium of 8 bacteria with minimal urease gene content, established a persistent new community that exhibited long-term reduction in fecal urease activity and ammonia production. ASF transplantation was associated with a decrease in morbidity and mortality in a murine model of hepatic injury. These results provide proof-of-concept that inoculation of a prepared host with a defined gut microbiota can lead to durable metabolic changes with therapeutic utility.

Figure 17:
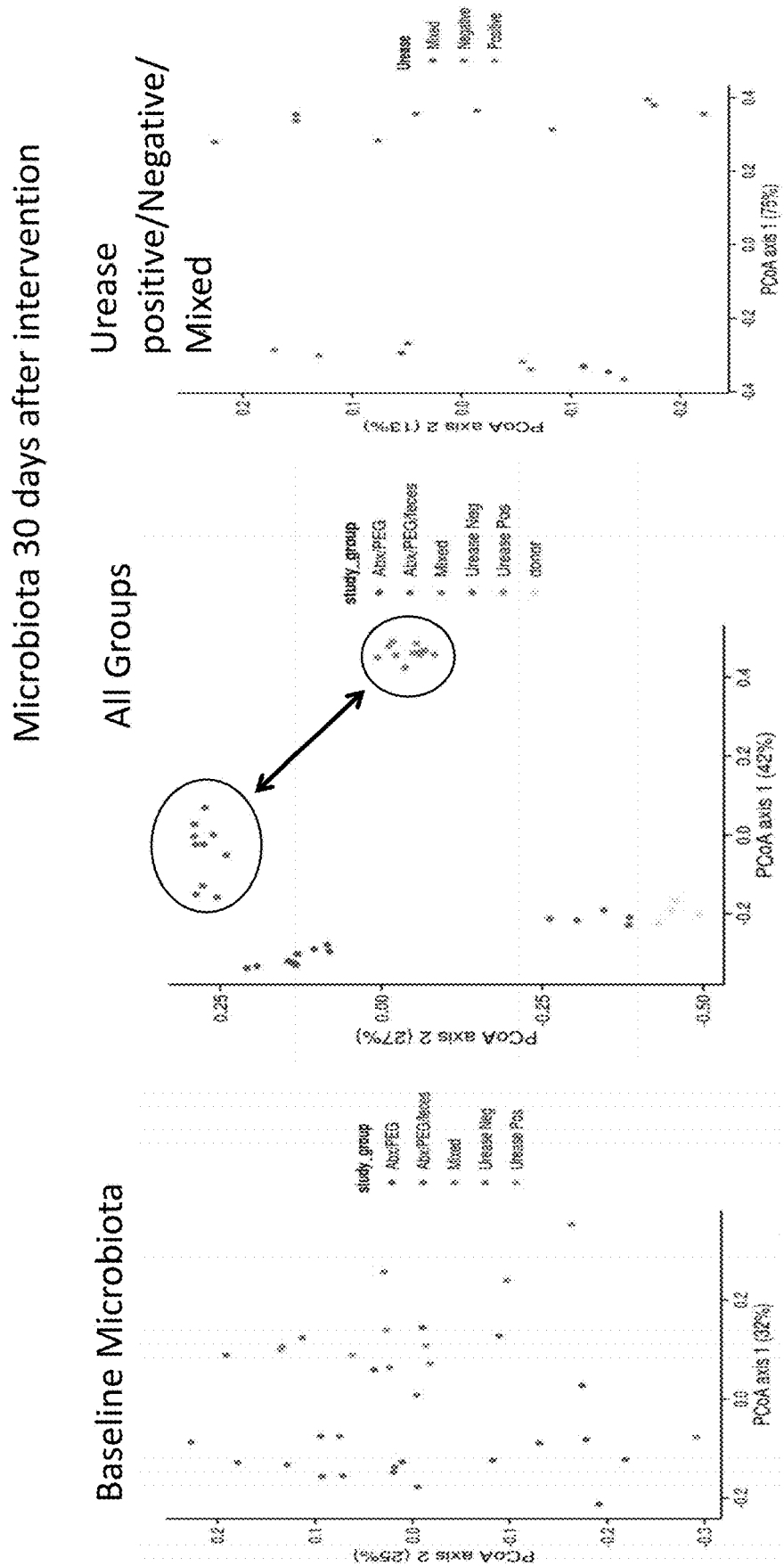
FIG. 17 shows reconfiguration of the gut microbiota by a single gene (urease) in an aerotolerant facultative anaerobic bacterial strain—*E. coli* MP-1. PCoA plots of the gut microbiota characterized by 16S rRNA gene sequencing in mice treated with Abx/PEG, Abx/PEG and inoculated with normal feces (Abx/PEG/feces, Donor feces labeled yellow), Abx/PEG and inoculated with urease negative *E. coli* MP1 (Urease Neg), Abx/PEG and inoculated with urease positive *E. coli* MP1 (Urease Pos), Abx/PEG and inoculated with a 1:1 mixture of urease negative and positive *E. coli* MP1 (Mixed). The composition of the gut microbiota before intervention shows no separation between the groups. Day 30 after inoculation there is a dramatic separation between the groups with a notable difference between mice inoculated with urease negative *E. coli* and mice inoculated with either urease positive *E. coli* or a mixture of urease positive and negative *E. coli*.
Figure 18:
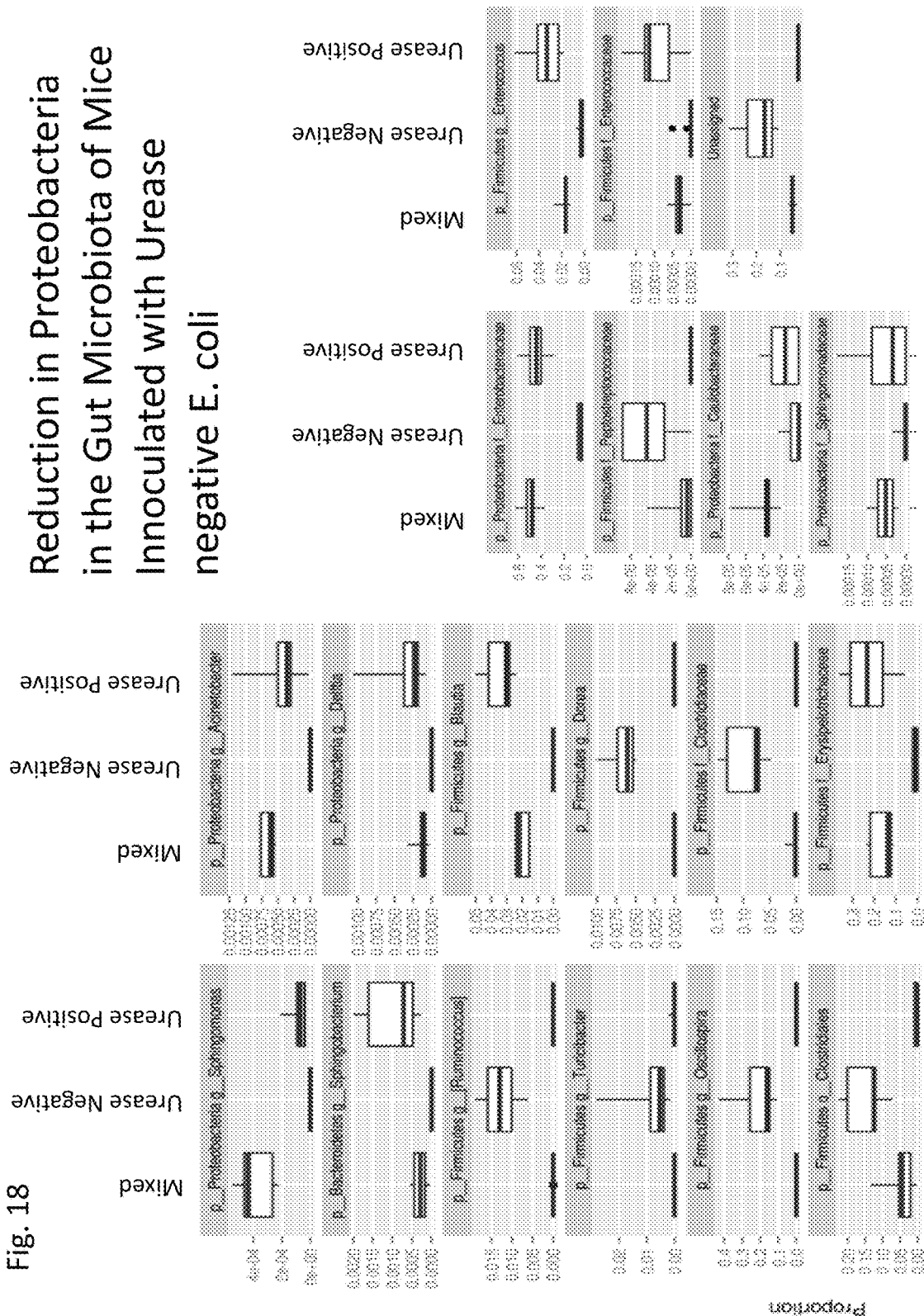
FIG. 18 demonstrates that innoculation with a urease negative vs. urease positive *E. coli* strain determines the levels of Proteobacteria (dysbiosis) in a properly prepared host. Relative abundance of various bacterial taxa in the feces of mice inoculated with urease negative, urease positive, or a mixture of urease negative and positive *E. coli* MP1. Dysbiotic bacteria from the Proteobacteria phylum[1-3] predominate in the feces of mice inoculated with urease positive *E. coli* MP1 (either alone or mixed with urease negative *E. coli*) where as more innocuous and/or beneficical taxa for the *Firmicutes phylum*[3-5] predominate in the feces of mice inoculated with urease negative *E. coli* MP1. All comparisons of statistically-significant after correction for multiple comparisons with a FDR of <0.05.

In the present example, we have determined that a single organism that is aerotolerant (a facultative anaerobe), *E. coli*, can engraft into the gut microbiota of a properly prepared host where the presence or absence of urease leads to dramatic differences in the reconfiguration of the resultant gut microbiota (FIGS. 16 and 17). *E. coli* engineered to express urease, lead to the development of a "dysbiotic" microbiota when inoculated into a properly prepare host featuring a predominance of Proteobacteria taxa where as *E. coli* lacking urease (the wild-type condition) nucleates the development of a more "healthy" microbiota with a predominance of *Firmicutes* featuring *Clostridia* taxa (FIG. 18). These findings are novel and of critical importance for several reasons.

Figure 13:
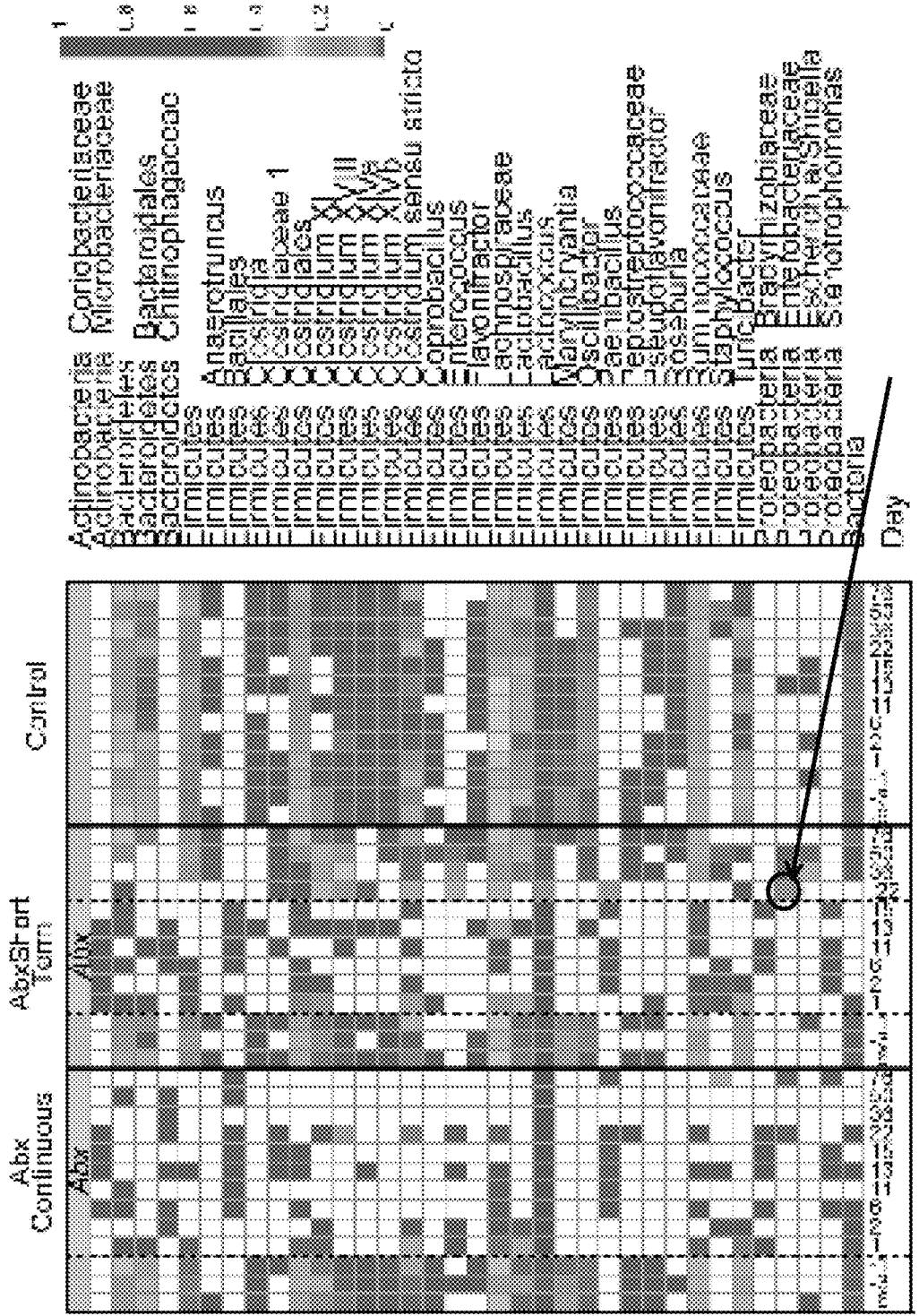
FIG. 13 shows a heat map indicating episodic variation and proliferation of fungi populations during antibiotic treatment in the murine gut. Succession in the return of the gut microbiota after treatment with oral antibiotics in mice reveals initial colonization with enterobacteraceae (aerotolerant organisms) that presumably consume oxygen leading to the anaerobic luminal environment of the gut and the growth of obligate anaerobic bacteria. This is similar to the succession of microbial communities in the gut of humans shortly after birth and throughout the first few weeks of life.
Figure 14:
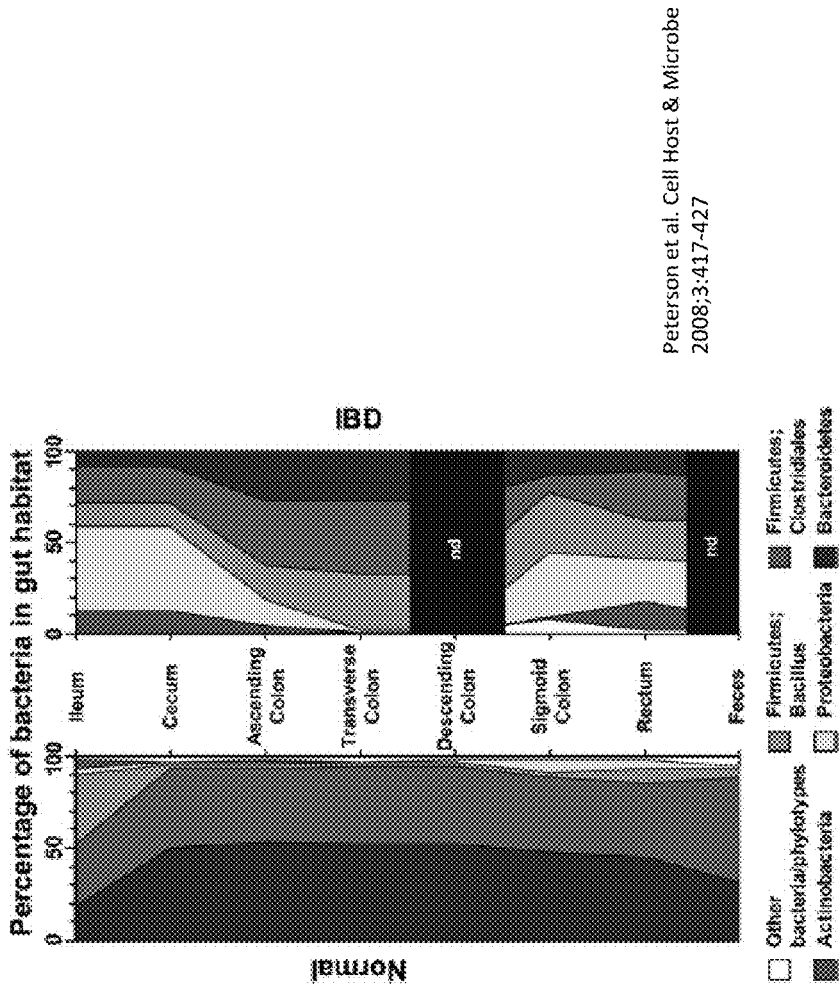
FIG. 14 shows that the dysbiotic microbiota in inflammatory bowel disease is predominant in aerotolerant Proteobacteria, taxa that may play a role in the chronicity of disease[1-3].

The use of an aerotolerant organism such as a facultative anaerobe is a preferentially advantageous modality to inoculate a host due to the higher levels of oxygen in the lumen of the gut (unpublished observations). The gut microbiota is a complex and densely populated community that exists within a dynamic environment determined by the host physiology. We characterize host determinants that distinguish the fecal from the mucosally-adherent microbiota. Using the phosphorescence quenching method and a specially designed intraluminal oxygen probe, we quantified oxygen levels in the gut of mice, showing that the average $pO_2$ values in the lumen are extremely low, e.g. <1 mmHg in the cecum[1]. These levels rise dramatically when bacterial load is reduced significantly by the treatment with antibiotic demonstrating that host intestinal tissue continuously delivers oxygen to the gut microbiota, the bacterial consumption of which results in a largely anaerobic gut lumen. We have also shown that the succession in the return of the gut microbiota after treatment with oral antibiotics in mice reveals initial colonization with enterobacteraceae (aerotolerant organisms) that presumably consume oxygen leading to the anaerobic luminal environment of the gut and the growth of obligate anerobic bacteria. This is similar to the succession of microbial communities in the gut of humans shortly after birth and throughout the first few weeks of life. See FIG. 13.

The use of an aerotolerant organism greatly simplifies the manufacturing process for the development of a product for human treatment. Additionally, no engineering of the bacterium is necessary as urease negative aerotolerant commensal organisms will be employed.

There is a sizable body of literature that the human counterpart of MP1 (the organism used in our study), known as E. coli Nissel, has physiologic benefits in animal models with modest effects in human studies. Our strategy should dramatically improve the efficacy of this and other urease negative probiotics.

This finding supports the notion that currently used urease negative (see tables below) probiotics might have enhanced beneficial effects when inoculated into a properly prepared host where they should reconfigure the composition of the gut microbiota into a new steady state therapeutically beneficial condition.

TABLE A

Previously characterized pro-biotic strains
Strain

| Strain |
|---|
| Lactobacillus acidophilus |
| L. acidophilus |
| L. acidophilus |
| L. acidophilus |
| Lactobacillus casei |
| L. casei Immunitas |
| Lactobacillus fermentum |
| Lactobacillus johnsonii |
| Lactobacillus paracasei |
| Lactobacillus plantarum |
| Lactobacillus reuteri |
| Lactobacillus rhamnosus |
| Lactobacillus salivarius |
| Lactobacillus lactis |
| Bifidobacterium lactis |
| Bifidobacterium longum |
| B. longum |
| Bifidobactenium breve |

TABLE B

| Probiotic strains | Urease content | Genomes queried |
|---|---|---|
| E. coli Nissle | No | 1 |
| Bifidobacterium breve | No | 1 |
| Bifidobacterium longum | No | 3 |
| Bifidobacterium infantis | Yes | 1 out of 2 |
| Lactobacillus acidophilus | No | 1 |
| Lactobacillus plantarum | No | 3 |
| Lactobacillus paracasei | No | 1 |
| Lactobacillus dubrueckii bulgaricus | No | 2 |
| Streptococcus thermophillus | Yes/No | 3 out of 4+/1 out 4− |
| Lactobacillus paracasei | No | 2 |
| Lactobacillus reuteri | No | 2 |
| Lactobacillus casei | No | 2 |
| Lactobacillus rhamnosus | No | 2 |

Notably, urease negative strains of S. thermophillus have been described in the literature[14,15] which would also be suitable for use in the present invention. We will identify and characterize additional E. coli strains (or other urease negative facultative anaerobes described above, see Table A and B) that do not have pathogenicity loci which may be more effective than the Nissle strain reducing dysbiosis to treat disease. While we use urease as the most obvious example of this and the shot-gun metagenomic data in IBD supports this concept, we will also be assessing whether alternative genes/pathways in bacteria that regulate bacterial nitrogen balance, can be used to alter the composition/function of the gut microbiota to treat disease.

Figure 19:
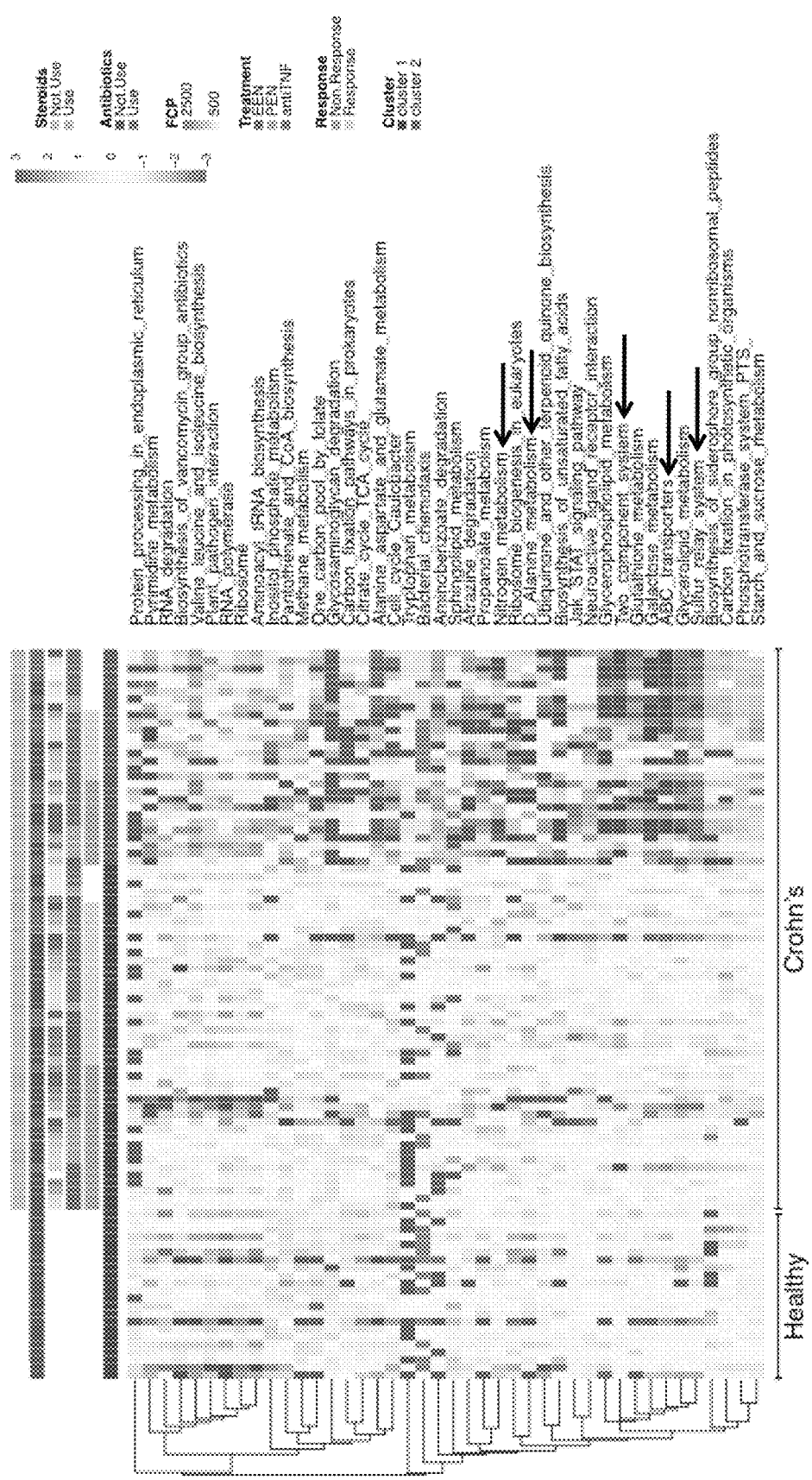
FIG. 19 provides a comparison of gene pathways present in samples from Crohn's disease subjects and healthy controls at baseline assessed by shotgun metagenomics. Heat map of pathways that differed significantly (q value<0.05) between healthy controls and Crohn's disease subjects at baseline. Each row was normalized by z-score. The gene content of the gut microbiota was compared to investigate possible different functionality in patients with Crohn's disease compared to healthy control subjects using HUMAnN. Differences were found between IBD and healthy controls in 42 of 163 pathways examined (data not shown). Gene pathways that participate in bacterial nitrogen utilization were associated with greater abundance in the microbiota of patients with Crohn's disease (see arrows).
Figure 20:
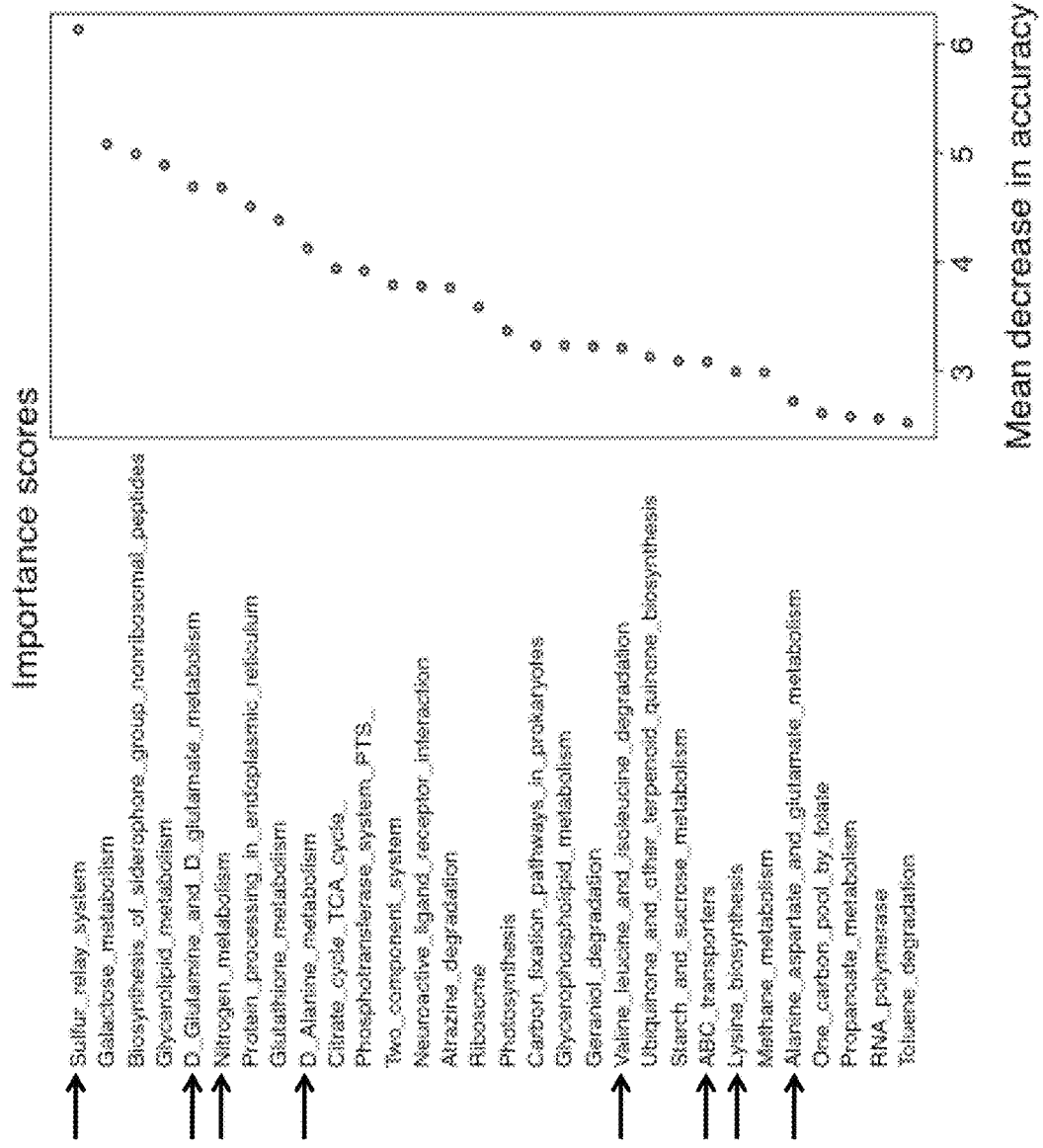
FIG. 20 shows the results when random forest was used to identify those pathways that best discriminated between healthy children and the Crohn's disease cohort at baseline. Samples could be sorted between the two categories with 87% accuracy using gene pathway data, comparable to partitioning achieved using bacterial taxonomic data. The top six most notable pathways related to sulfur relay systems, galatose metabolism, biosynthesis of siderophores, glycerolipid metabolism, glutamine/glutamate metabolism, and nitrogen metabolism were notably increased among the children with Crohn's disease.
Figure 21:
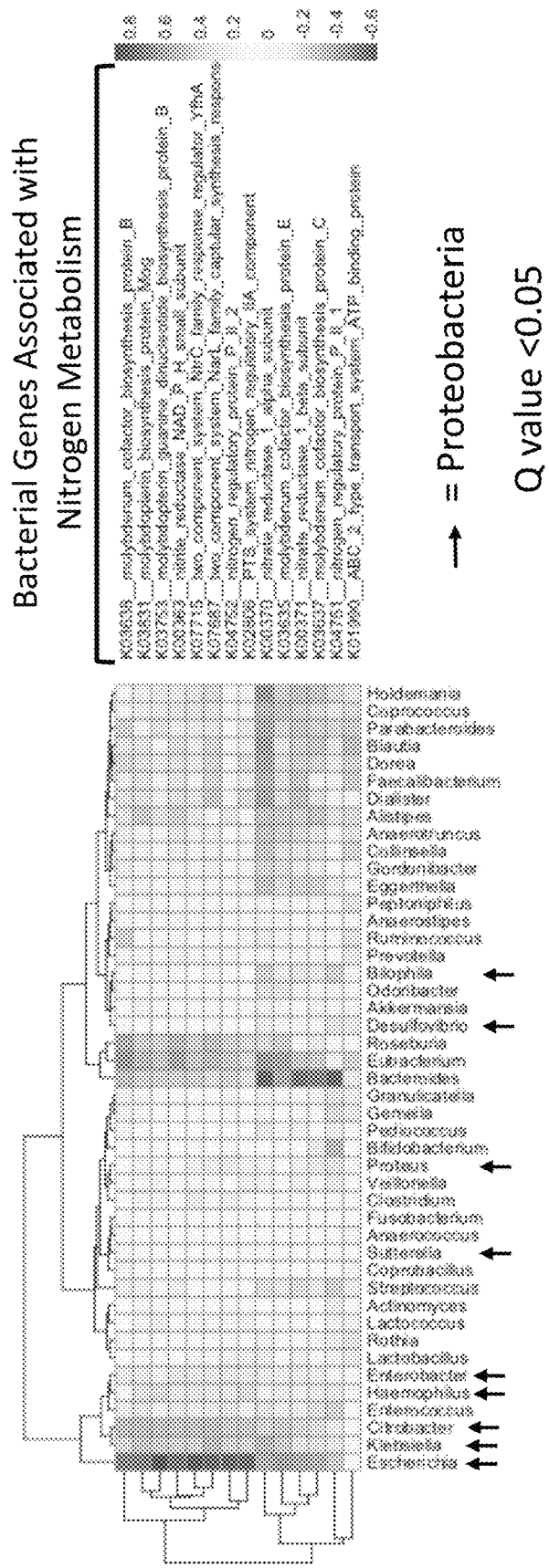
FIG. 21 shows that 14 bacterial genes involved in nitrogen flux/metabolism in bacteria with significantly increased abundance in Crohn's disease (Q value<0.05) are, in general, positively associated with bacterial belonging to the Proteobacteria phylum (see arrows). The association is particularly positive for *E. coli* suggesting that nitrogen flux, perhaps through urease positive strains of *E. coli*, may be deleterious in patients with Crohn's disease. For example, the master regulator of the nitrogen stress response in enterobacteria is the NtrC two-component system[6,7], a pathway when mutated, significantly alters colonization competition efficiency in *E. coli*[8]. Other genes involve nitrate/nitrite respiration pathways[9]. Combined with FIGS. 19 and 20, this data provides evidence in humans that nitrogen metabolism by the gut microbiota may play an important role in the development of dysbiosis dominated by Proteobacteria in patients with Crohn's disease. The release of ammonia by bacterial urease activity may be a critical factor in regulating the composition of the gut microbiota since ammonia is a principal source of nitrogen for bacteria.

We have data showing a prominent signature associated with bacterial nitrogen metabolism associated with the dysbiotic signature of the gut microbiota in human patients with IBD. Indeed, the Proteobacteria Phylum may be particularly sensitive to nitrogen sources in the environment such as ammonia. These finding support the broader notion that we can develop methods to alter microbial nitrogen balance to modify the gut microbiome as shown in FIGS. 19, 20, and 21. Gene pathway analysis supports the notion that the gut microbiota responds to gut environmental stressors principally through the modification of metabolism. Gene pathways associated with IBD and dysbiosis included "sulfur relay systems" and "nitrogen metabolism", both of which are involved in bacterial nitrogen utilization, a prominent phylogenetic signature of the dysbiotic microbiota[1], particularly Proteobacteria[16]. The sulfur relay system provides sulfur via L-cysteine desulfurase for biosynthesis of molybdenum cofactor (Moco), as well as other biomolecules such as thiamin, iron-sulfur (FeS) clusters, and thionucleosides[17]. Specifically, Moco is responsible for catalyzing oxo-transfer reactions in the bacterial metabolism of nitrogen, sulfur, and carbon compounds[18]. Moco generically includes most molybdenum-based cofactors that contain a tricyclic pterin (molybdopterin), which are all molybdenum-based cofactors with the lone exception of the iron-molbydenum (FeMo) cofactor of nitrogenase. This FeMo cofactor is the most commonly distributed nitrogenase and is most efficient in converting $N_2$ to $NH_4^+$ in diazotrophic prokaryotes[19]. While nitrogen fixing capabilities are found across a wide array of prokaryotic phyla, diazotrophic species are by far most common amongst Proteobacteria, with some identified in the human gut[20]. Alternatively, Moco may play a role in various nitrate reduction pathways associated with nitrogen respiration in the setting of intestinal inflammation[21]. While the shifts in both community structure and gene expression may be linked to a variety of factors, the predominance of the sulfur relay system in the gut microbiome of patients with Crohn's disease emphasizes the possible importance of nitrogen metabolism in the development of the dysbiotic microbiota. Indeed, in FIG. 21, we provide evidence for 14 specific bacterial genes associated with nitrogen flux that show enriched association with bacteria belonging to the Proteobacteria phylum.

Figure 15:
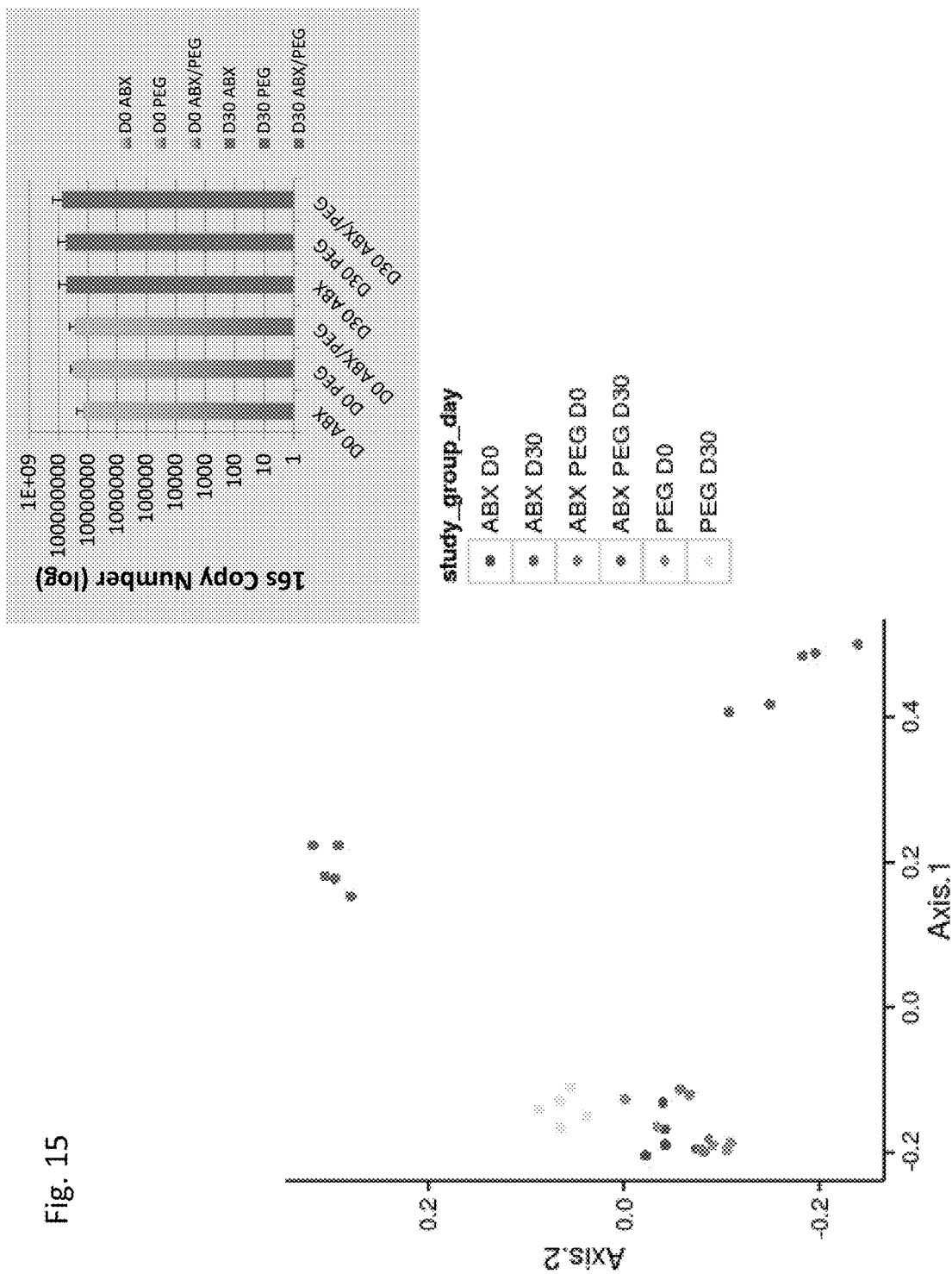
FIG. 15 provides data showing that treatment with either antibiotics or antibiotics/PEG, but not PEG alone, leads to the spontaneous reconfiguration of the gut microbiota in mice (PCoA plot of 16S rRNA gene sequencing results). Gray Box: 16S copy number showing equivalent abundance of bacteria at day 30 after treatment.
Figure 22A:
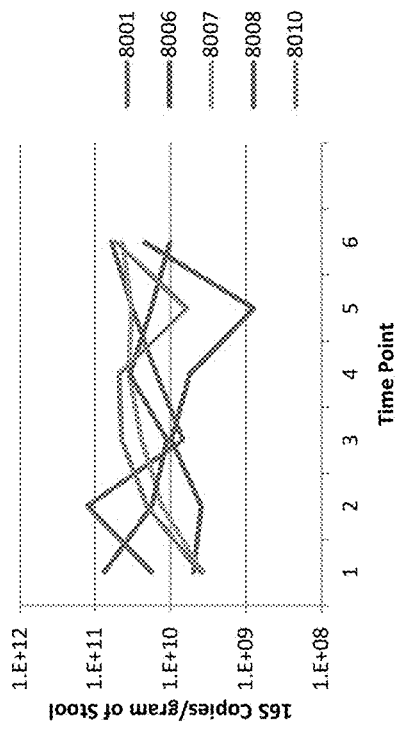
FIGS. 22A-22B demonstrate that not all antibiotics tested are effective in altering the composition and/or bacterial load of the gut microbiota in humans. There was no decrease in bacterial load in healthy human subjects treated with a combination of three oral antibiotics (rifaximin, trimethoprim-sulfamethoxazole, and flagyl) over three days (2.41× $10^{10}$ copies per gram of stool vs. 3.16×$10^{10}$ copies per gram of stool, p=0.68.
Figure 22B:
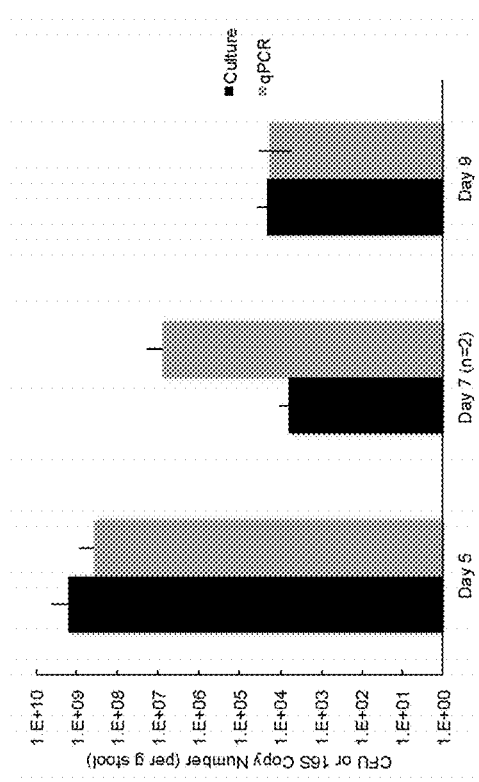

We now provide evidence in humans that the combination of vancomycin, neomycin, together with a polyethylene glycol (PEG) bowel purge, can reduce the load of culturable gut bacterial by over 100,000-fold. This is equivalent to the effectiveness in our murine models. Importantly, not all antibiotics significantly alter the human gut microbiota and a PEG purge enhances the action of antibodies in a significant way. Treatment of five subjects with three antibiotics (rifaximin, trimethoprim-sulfamethoxazole, and metronidazole) over three days showed had a surprisingly small effect on the composition of the gut microbiota with no effect of bacterial load as quantified by 16S gene copy number (FIGS. 15 and 22A). However, using a similar protocol as our mouse studies with two Abx (vancomycin and neomycin) and PEG, caused a dramatic reduction in both culturable bacteria and 16S gene copy number of approximately four to five logs after 72 hours in humans (FIG. 22B), similar to the response in mice (Shen et al., 2015). The difference between a five log decrease in culturable bacteria and a 2 log decrease in 16S gene copy number at 48 hours, prior to gut purge with PEG, likely represents residual DNA in the gut lumen from nonviable bacteria. These results suggest that a specific antibiotic/PEG protocol may enhance preparation of the human gut for inoculation and engineering of the gut microbiota.

Many current probiotics are all facultative anaerobes such as various strains of *lactobacillus* and *E. coli*. Many show marginal beneficial effects in human studies. However, none of them have been shown to remain in the intestinal environment and/or have a significant effect on the composition and/or function of the gut microbiota. Based on our data whereby a single facultative anaerobe (*E. coli*) can engraft at comparatively high levels and have a dramatic effect on the composition of the gut microbiota when inoculated into a prepared host, it is very likely that other facultative anaerobic organisms, many that are currently on the market being sold as "probiotics" as supplements, can have a more pronounced effect on the gut microbiota with greater beneficial effects on human health if inoculated into a patient who has been pretreated with oral antibiotics and polyethylene glycol (PEG).

Materials and Methods for Example 7
Animals

All animal experiments were performed according to IACUC-approved protocols, with mice housed in specific pathogen-free conditions and maintained on a 12 hr light/dark cycle. The diet used in the studies was AIN-76 (Rodent Diet D10001, Research Diets). For the microbiota colonization experiments, pretreated conventional mice were prepared for inoculation by oral delivery of ABX in the drinking water (1 g aspartame, 0.1 g vancomycin, and 0.2 g neomycin in 200 ml sterile water) for 72 hours. During the final 12 hours, the water supply was exchanged with a 10% PEG solution (Merck), and the mice were fasted. For the MP1 and Nissle experiments, the mice were then inoculated daily with the desired *E. coli* strains by oral gavage for 5 days. For the MP1 experiments, a strain of commensal mouse *E. coli*, MP1, was isolated and genetically engineered to express urease as well as a fluorescent marker (either GFP or MCherry). For the Nissle experiments, the wild-type strain of *E. coli* Nissle was used. Fecal pellets were collected for bacterial taxonomic and biochemical analyses at the time points indicated in the figures.

Abx/PEG: Conventionally reared C57BL/6 mice were treated with either a combination of oral antibiotics (vancomycin+neomycin suspended in drinking water) for 72 hours, polyethylene glycol for 12 hours, or both. 16s rRNA qPCR was performed for total bacterial counts at baseine, day 30, and day 80. 16S rRNA gene sequencing was performed at baseline and day 30 post-intervention to characterize the composition of the gut microbiota. Fecal ammonia and fecal urease levels were also measured at baseline and at days 30 and 80 post-intervention FARMM Stool Studies: Subjects recruited for the FARMM study provide stool samples prior to receiving antibiotics, after receiving antibiotics but before PEG, and after both treatments. Serial dilutions of fresh stool are then cultured on anaerobic GMM plates and colony counts are obtained. 16s qPCR was also performed for total bacterial counts. MP1: Conventionally reared C57BL/6 mice were treated with a combination of oral antibiotics (Abx) and polyethylene glycol (PEG) to deplete the endogenous gut microbiota. A strain of commensal mouse *E. coli*, MP1, was isolated and genetically engineered to express urease. The urease gene cluster in pMID1010 (from *Proteus Mibrabilus*) was subcloned in the CRIM vector for integration at attHK022 per established protocols (PMID: 24563035). Fluorescent tags also inserted at the attλ site of the MP1 genome for Urease Positive (Mcherry) vs Urease Negative (GFP) MP1. Serial dilutions of fresh stool were then cultured on tetracycline-LB plates and colony counts were obtained initially weekly then monthly. Both the wild-type urease negative MP1 strain (Ure−) and the engineered urease positive strain (Ure+) were inoculated into mice consecutively for 5 days after the depletion of the native gut microbiota with Abx/PEG. Nissle: The MP1 process was repeated with a human strain of *E. coli*, Nissle, which was inoculated into different mice consecutively for 5 days after depletion of the native gut microbiota with Abx/PEG. Colony counts were performed weekly on serial stool dilutions to measure the durability of MP1 and Nissle colonization. 16S rRNA gene sequencing was performed at baseline and at Day 29 post-gavage to characterize the composition of the gut microbiota.

FARMM

The FARMM study recruited healthy volunteers ages 18-60 for either a 15-day inpatient stay or 15 days outpatient (for vegan participants who self-reported being vegan for 6 months or more). Non-vegan participants were randomized to consume either an omnivore diet or a defined formula diet for the entire 15 days. The defined formula diet used for FARMM was Modulen IBD, a formula given for the dietary management of active Crohn's disease. Vegan participants maintained their usual diet. Stool, urine, blood, and rectal biopsies were collected throughout the 15 days. Diet history data was collected via a diet history questionnaire or a food diary and dietary recalls. A Sitz Marker study was completed to track transit time through the digestive track. Participants underwent a bowel cleansing on days 6-8 which included a course of antibiotics administered every 6 hours for three days, as well as 4 L of a commonly used polyethylene glycol solution on day 7. Subjects recruited for the FARMM study provided stool samples prior to receiving antibiotics, after receiving antibiotics but before PEG, and after both treatments. Serial dilutions of fresh stool were then cultured on anaerobic GMM plates and colony counts were obtained.

Quantitative PCR

Quantification of bacterial 16S rRNA genes was performed by real-time PCR utilizing TaqMan hydrolysis probes on a StepOne Plus (Applied Biosystems), as described previously (PMID: 24831685, PMID: 21680950, PMID: 19940845, PMID: 8428640). The level of detection (LOD) was determined using a standard curve for the quantitative PCR (qPCR) assay and was based on the number of copies present in the lowest 16S qPCR standard that is different from the no-DNA standard and falls within the linear range of the analysis.

$^{15}$N Experiment Fecal Microbial Transplant (FMT) using ASF (without urease activity) was performed in conventionally reared C57BL/6 mice. These mice were compared to mice that were continuously treated with antibiotics (vancomycin and neomycin) as well as control mice. After ASF transplant, all groups were gavaged with either $^{15}$NH$_4$Cl or $^{15}$N$^{15}$N-urea. Plasma and fecal pellets were then collected at baseline and at various points after FMT and treatment with $^{15}$N compounds and specimens underwent analysis for ammonia, urea, and amino acids (AAs) via gas chromatography-combustion-isotope ratio mass spectrometry (GC-C-IRMS) in collaboration Dr. Marc Yudkoff's lab at the Children's Hospital of Philadelphia using established preparation and analytical techniques.

Microbial Community Analysis

The sequenced 16S reads were analyzed using the QIIME software package (Caporaso 2010) and the R programming language (R Core Team 2014). Reads were removed from the analysis if they did not match a 12-base golay-barcode 1 or fewer errors, if the reads failed to overlap by 35-bases, if the overlapped region differed by more than 15%, or if they had more than 3 base calls below Q20. Operational taxonomic units (OTUs) were created by clustering the reads at 97% identity using UCLUST (Edgar 2010). Representative sequences from each OTU were aligned using PyNAST (Caporaso 2010b), and a phylogenetic tree was inferred using FastTree v. 2.1.3 (Price 2010) after applying the standard Lane mask for 16S sequences (Lane 1991). Pairwise UniFrac distances were computed using QIIME (Lozupone 2005), and permutational tests of distance were performed using the vegan library for the R programming language (Oksanen 2013). Permutations were restricted to randomize treatments by cage, following the procedure recommended by Anderson (Anderson 2001). Principal coordinates analysis was performed with the APE library for R (Paradis 2004). Taxonomic assignments were generated by the UCLUST consensus method of QIIME 1.8 (Bokulich, in publication), using the GreenGenes 16S database v. 13_8 (McDonald 2012).

References for Example 7

1. Frank D N, St Amand A L, Feldman R A, et al. Molecular-phylogenetic characterization of microbial community imbalances in human inflammatory bowel diseases. Proc Natl Acad Sci USA 2007; 104:13780-5.
2. Garrett W S, Gallini C A, Yatsunenko T, et al. Enterobacteriaceae act in concert with the gut microbiota to induce spontaneous and maternally transmitted colitis. Cell Host Microbe 2010; 8:292-300.
3. Sartor R B. Microbial influences in inflammatory bowel diseases. Gastroenterology 2008; 134:577-94.
4. Atarashi K, Tanoue T, Shima T, et al. Induction of colonic regulatory T cells by indigenous *Clostridium* species. Science 2011; 331:337-41.
5. Atarashi K, Tanoue T, Oshima K, et al. Treg induction by a rationally selected mixture of *Clostridia* strains from the human microbiota. Nature 2013; 500:232-6.
6. Brown D R, Barton G, Pan Z, et al. Nitrogen stress response and stringent response are coupled in *Escherichia coli*. Nat Commun 2014; 5:4115.
7. Reitzer L. Nitrogen assimilation and global regulation in *Escherichia coli*. Annu Rev Microbiol 2003; 57:155-76.
8. Lasaro M, Liu Z, Bishar R, et al. *Escherichia coli* isolate for studying colonization of the mouse intestine and its application to two-component signaling knockouts. J Bacteriol 2014; 196:1723-32.
9. Moreno-Vivian C, Cabello P, Martinez-Luque M, et al. Prokaryotic nitrate reduction: molecular properties and functional distinction among bacterial nitrate reductases. J Bacteriol 1999; 181:6573-84.
10. Shen T D, Albenberg L, Bittinger K, et al. Engineering the gut microbiota to treat hyperammonemia. J Clin Invest 2015; 125:2841-2850.
11. Schnabl B, Brenner D A. Interactions between the intestinal microbiome and liver diseases. Gastroenterology 2014; 146:1513-24.
12. Qin N, Yang F, Li A, et al. Alterations of the human gut microbiome in liver cirrhosis. Nature 2014; 513:59-64.
13. Arumugam M, Raes J, Pelletier E, et al. Enterotypes of the human gut microbiome. Nature 2011; 473:174-80.
14. Mora D, Fortina M G, Parini C, et al. Genetic diversity and technological properties of *Streptococcus thermophilus* strains isolated from dairy products. J Appl Microbiol 2002; 93:278-87.
15. Monnet C, Pernoud S, Sepulchre A, et al. Selection and properties of *Streptococcus thermophilus* mutants deficient in urease. J Dairy Sci 2004; 87:1634-40.
16. Forchhammer K. Glutamine signalling in bacteria. Front Biosci 2007; 12:358-70.
17. Leimkühler S. The Biosynthesis of the Molybdenum Cofactor in *Escherichia coli* and Its Connection to FeS Cluster Assembly and the Thiolation of tRNA. Advances in Biology 2014; 2014:1-21.
18. Iobbi-Nivol C, Leimkuhler S. Molybdenum enzymes, their maturation and molybdenum cofactor biosynthesis in *Escherichia coli*. Biochim Biophys Acta 2013; 1827: 1086-101.
19. Hernandez J A, George S J, Rubio L M. Molybdenum trafficking for nitrogen fixation. Biochemistry 2009; 48:9711-21.
20. Bergersen F J, Hipsley E H. The presence of N2-fixing bacteria in the intestines of man and animals. J Gen Microbiol 1970; 60:61-5.
21. Winter S E, Winter M G, Xavier M N, et al. Host-derived nitrate boosts growth of *E. coli* in the inflamed gut. Science 2013; 339:708-11.

Example 8

Procedure for Designing Human Bacterial Communities for Treating Hyperammonemia and Other Forms of Dysbiosis While the altered gut micriobiota described herein is useful for reducing urease production from the gut, additional novel defined microbial consortia can be obtained using the following exemplary steps. Stool is collected from adults in robust health who meet the following criteria and none of the following.
  a) Consumption of prebiotics or probiotics in the 4 weeks prior to sample collection. This will include products specifically marketed as prebiotics or probiotics, including yogurt with live bacteria.
  b) Diagnosis with inflammatory bowel disease, celiac disease, or other chronic intestinal disorders or any other chronic medical conditions.
  c) Baseline bowel frequency less than every 2 days or greater than 3 times daily. Normal bowel frequency is every $3^{rd}$ day to 3 times per day.[15-18] Although unknown, stool frequency could be related to the microbiome composition.[19-21]
  d) Prior bowel resection surgery. It is unknown how prior bowel resection surgery may influence the microbiome composition, hence we will exclude these subjects.
  e) Use of antibiotics in the prior 6 months. A small proportion of bacteria may require 6 months to recover after treatment with antibiotics.[22]
  f) Use of antacids or NSAIDs in the preceding 2 weeks. NSAIDs have been associated with *C. difficile* colitis, although whether this is causative and whether this is mediated through changing the fecal microbiota composition is unknown.[23] Antacids could potentially alter the gut microbiota by changing the acid milieu or by altering fecal transit time.
  g) Use of any of the following medications in the 4 weeks prior to randomization: proton pump inhibitors (PPI), histamine receptor antagonists, narcotics, tricyclic antidepressants, anticholinergics (e.g., hyoscamine), metoclopramide, anti-diarrhea medications, laxatives. PPIs and other acid suppression medications are thought to potentially alter the intestinal microbiota.[23-26] Antacids could potentially alter the gut microbiota by changing the acid milieu or by altering fecal transit time. Other medications (such as narcotics) that could alter fecal transit time will be prohibited. Within 2-4 weeks of discontinuing these medications, the composition of the gut microbiota is expected to return to normal.[27,28]
h) HIV infection, AIDS, or other known conditions resulting in immunosuppression.
i) Participant has experienced diarrhea within the two weeks prior to the stool collection. Diarrhea is defined as a change in bowel habits with an increased frequency or loose stools such that the stool could not be lifted with a fork.
j) Conditions or medications that interfere with the potential participant's completion of the study protocol or that may negatively alter the potential participant's samples.

Once obtained, bacterial strains are purified by repeated rounds of streaking and limiting dilution under anaerobic conditions on multiple types of media. They are then tested for survival at after freezing at −80° C. and subsequent thawing. After phylogenetically characterizing the isolated strains by sequencing of 16S rRNA gene sequences, information on Genus and species attribution is used to ascertain the probability of containing urease genes by comparison to databases of complete bacterial genome sequences. Suitable strains are then formulated into communities with structures resembling resilient human communities from healthy individuals (containing multiple *Firmicutes*, Bacteriodetes, and other taxa), but using only strains identified as lacking urease genes. Human strains are also evaluated by comparison to murine ASF. Specifically, because Parabacteriodes was predominant in ASF in colon, this approach will ensure that members of the Parabacteriodes/Bacteroides group are represented in engineered communties.

Following identification of suitable consortia, these are tested in mice for ability to persist in a suitably prepared animal. The newly identified consortia can then be assess for alteration of the disease parameters targeted for alleviation. For example, in the present case, the consortia are tested for ability to lower fecal ammonia level and/or in rescue in models of ammonia toxicity.

Selected bacterial strains are characterized by near-complete genome sequencing and the sequences are assessed for the presence or absence certain types of genes, e.g., urease genes, antibiotic resistance genes, and or virulence gene representation. Once satisfied that the strains meet these criteria, strains can be tested functionally for ureases activity and/or for antibiotic resistance to identify antibiotic classes to which all strains are sensitive. Should any adverse gene content be identified, the consortia will be edited to remove any members with adverse gene content or activities as set forth above, then the final community retested.

Using the steps outlined above, we have identified a seven member community that passes these criteria and includes: *Paraprevotella clara*, *Bifidobacterium longum*, *Collinsella aerofaciens*, *Coprococcus comes*, *Dorea longicatena*, *Bacteroides eggerthii*, and *Bacteroides vulgatus*.

Accordingly, this community can be used to advantage in human subjects in the methods of treatment described herein.

Using the methodology described herein to characterize isolated strains, it is clear that any bacteria lacking urease, antibiotic resistance genes and virulence genes is a candidate for use in the compositions and methods described herein.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for altering gut microbiota to reduce urease gene content or activity via reducing or eliminating urease producing bacteria from the gut in order to reduce ammonia production therefrom, in a subject in need thereof, the method comprising;
    a) administering to the subject an effective amount of one or more antibiotics sufficient to reduce the population of bacteria in the gut microbiota to a level suitable for repopulation of newly introduced bacteria, wherein one or more antibiotics is administered for at least about 48, 72, or 96 hours prior to the administration of a composition comprising *Paraprevotella clara*, *Bifidobacterium longum*, *Collinsella aerofaciens*, *Coprococcus comes*, *Dorea longicatena*, *Bacteroides eggerthii str.*, and *Bacteroides vulgates* bacteria, said bacteria having no urease gene content or urease activity;
    b) administering said composition to the subject, under conditions wherein said bacteria colonize and populate the gut, thereby reducing urease gene content, or activity or both in gut microbiota and ammonia production in the gut of the subject.

2. The method of claim 1, wherein said subject is a human and has a disease associated with an undesirable gut microbiome, said composition alleviating symptoms associated with said undesirable gut microbiome, wherein said administration of said composition is via a route selected from the group consisting of by endoscopy, by enteroscopy, by colonoscopy, a nasoduodenal catheter, an enema and orally in a consumable capsule or pill and the composition further comprises one or more of *Clostridium* sp., *Lactobacillus* sp., *Lactobacillus murinus*, *Mucispirillum schaedleri*, *Eubacterium plexicaudatum*, *Firmicutes bacterium*, *Clostridium* sp., and *Parabacteroides* sp.

3. The method of claim 1, comprising administering an effective amount of a purgative agent to the subject between steps a) and b), thereby purging the intestines of said subject prior to administration of said composition.

4. The method of claim 3, wherein said subject is administered antibiotics and a purging agent prior to administration of said composition, said antibiotic being one or both of neomycin and vancomycin, and said purging agent being administered for at least about 12-36 hours prior to the administration of the composition.

5. The method of claim 3, wherein said purgative agent is selected from the group consisting of polyethene glycol (PEG), magnesium citrate, sodium picosulphate plus magnesium citrate, PEG plus ascorbic acid, and sodium phosphate.

6. The method of claim 1, wherein said composition comprises one or more additional bacteria belonging to a genus selected from the group consisting of *Bifidobacterium*, *Bacteroides*, *Tannerella*, *Parabacteroides*, *Bacillus*,

*Lactobacillus, Anaerostipes, Blautia, Coprococcus, Dorea, Clostridium XI, Collinsella,* and *Paraprevotella.*

7. The method of claim 2, wherein the disease is a metabolic disorder selected from the group consisting of Hyperammonemia, and Transient Hyperammonemia of the Newborn.

8. The method of claim 2, wherein the disease is *Clostridium difficile* colitis, inflammatory bowel disease, cirrhosis, or hepatic encephalopathy.

9. The method of claim 1 or claim 2, wherein the level of bacteria repopulating the gut is monitored by assessing a parameter selected from the group consisting of 16S rRNA copy number, 16S rRNA gene sequencing, fecal urease levels, fecal or circulating amino acids, biogenic amines, fecal ammonia levels, and circulating ammonia levels.

* * * * *

UNITED STATES PATENT AND TRADEMARK OFFICE
CERTIFICATE OF CORRECTION

PATENT NO. : 10,058,576 B2
APPLICATION NO. : 15/090609
DATED : August 28, 2018
INVENTOR(S) : Frederic Bushman et al.

It is certified that error appears in the above-identified patent and that said Letters Patent is hereby corrected as shown below:

In the Specification

Column 1, Lines 20-24, delete the following paragraph:
"This work was supported by the following grants from the National Institutes of Health, Grant Nos: UH2/3 DK083981 and DK089472. The government has certain rights in the invention."

And insert the following paragraph in its place:
--This invention was made with government support under grant number DK083981 by the National Institutes of Health. The government has certain rights in the invention.--

Signed and Sealed this
Second Day of April, 2019

Andrei Iancu
*Director of the United States Patent and Trademark Office*